(12) United States Patent
Albertsson et al.

(10) Patent No.: US 11,771,572 B2
(45) Date of Patent: Oct. 3, 2023

(54) PROSTHETIC FEET HAVING HEEL HEIGHT ADJUSTABILITY

(71) Applicant: Össur Iceland ehf, Reykjavik (IS)

(72) Inventors: Aron Kristbjorn Albertsson, Hafnarfjordur (IS); Maria Gudrun Sveinbjornsdottir, Mosfellsbaer (IS); Rowan Patrick Robinson Cain, Kopavogur (IS); Jeroen Nijman, Reykjavik (IS); David Sandahl, Reykjavik (IS); Larus Gunnsteinsson, Reykjavik (IS)

(73) Assignee: Össur Iceland ehf, Reykjavik (IS)

(*) Notice: Subject to any disclaimer, the term of this patent is extended or adjusted under 35 U.S.C. 154(b) by 111 days.

(21) Appl. No.: 17/035,418

(22) Filed: Sep. 28, 2020

(65) Prior Publication Data
US 2021/0077281 A1    Mar. 18, 2021

Related U.S. Application Data

(63) Continuation of application No. 15/828,944, filed on Dec. 1, 2017, now Pat. No. 10,821,007.
(Continued)

(51) Int. Cl.
*A61F 2/66*    (2006.01)
*A61F 2/74*    (2006.01)
(Continued)

(52) U.S. Cl.
CPC .............. *A61F 2/6607* (2013.01); *A61F 2/68* (2013.01); *A61F 2/74* (2021.08); *A61F 2/744* (2021.08);
(Continued)

(58) Field of Classification Search
CPC ............ A61F 2/6607; A61F 2002/6621; A61F 2002/6628
(Continued)

(56) References Cited

U.S. PATENT DOCUMENTS 25,238 A    8/1859   Bly
53,931 A    4/1866   Weston et al.
(Continued)

FOREIGN PATENT DOCUMENTS

CA    2 127 691    5/1994
CA    2234362      4/1998
(Continued)

OTHER PUBLICATIONS

Burden et al., Numerical Analysis, 2$^{nd}$ edition (1981): Prindle, Weber * Schmidt; p. 3.
(Continued)

*Primary Examiner* — David H Willse
(74) *Attorney, Agent, or Firm* — Knobbe, Martens, Olson & Bear LLP

(57) ABSTRACT

Prosthetic feet that allow for heel height adjustment and/or provide metatarsal joint functionality to more closely mimic natural human feet are provided. A prosthetic foot can include an ankle module having a locking mechanism configured to lock the heel at a particular height. The prosthetic foot can also include a toe region that adapts to varying heel heights. The ankle module and/or locking mechanism can be adjusted, controlled, and/or locked via a hydraulic mechanism. The toe region can curve upward relative to a portion of the foot proximal of the toe region.

20 Claims, 19 Drawing Sheets

Related U.S. Application Data

(60) Provisional application No. 62/428,942, filed on Dec. 1, 2016.

(51) Int. Cl.
  *A61F 2/62* (2006.01)
  *A61F 2/68* (2006.01)
  *A61F 2/50* (2006.01)

(52) U.S. Cl.
  CPC ....... *A61F 2/748* (2021.08); *A61F 2002/5001* (2013.01); *A61F 2002/502* (2013.01); *A61F 2002/5018* (2013.01); *A61F 2002/5072* (2013.01); *A61F 2002/6614* (2013.01); *A61F 2002/6621* (2013.01); *A61F 2002/6628* (2013.01); *A61F 2002/6642* (2013.01); *A61F 2002/6657* (2013.01); *A61F 2002/6664* (2013.01); *A61F 2002/6827* (2013.01); *A61F 2002/6854* (2013.01)

(58) Field of Classification Search
  USPC .......................................................... 623/54
  See application file for complete search history.

(56) References Cited

U.S. PATENT DOCUMENTS

| | | |
|---|---|---|
| 56,983 A | 8/1866 | Nicholas |
| 57,666 A | 9/1866 | Bly |
| 368,580 A | 8/1887 | Frees |
| 487,697 A | 12/1892 | Ehle |
| 534,198 A | 2/1895 | Chapman |
| 619,731 A | 2/1899 | Doerflinger et al. |
| 808,296 A | 12/1905 | Merrick |
| 809,876 A | 1/1906 | Wilkins |
| 817,340 A | 4/1906 | Rosenkranz |
| 2,183,076 A | 12/1939 | Kaiser |
| 2,197,093 A | 4/1940 | Campbell |
| 2,315,795 A | 4/1943 | Johnson et al. |
| 2,357,893 A | 9/1944 | Harrington |
| 2,594,945 A | 4/1952 | Lucas et al. |
| 2,692,392 A | 10/1954 | Bennington et al. |
| 2,731,645 A | 1/1956 | Woodall |
| 3,551,914 A | 1/1971 | Woodall |
| 3,784,988 A | 1/1974 | Trumpler |
| 3,874,004 A | 4/1975 | May |
| 4,007,497 A | 2/1977 | Haupt |
| 4,360,931 A | 11/1982 | Hampton |
| 4,387,472 A | 6/1983 | Wilson |
| 4,547,913 A | 10/1985 | Phillips |
| 4,636,220 A | 1/1987 | Ziegelmeyer |
| 4,718,913 A | 1/1988 | Voisin |
| 4,822,363 A | 4/1989 | Phillips |
| 4,892,553 A | 1/1990 | Prahl |
| 4,892,554 A | 1/1990 | Robinson |
| 4,959,073 A | 9/1990 | Merlette |
| 5,019,109 A | 5/1991 | Voisin |
| 5,037,444 A | 8/1991 | Phillips |
| 5,062,859 A | 11/1991 | Naeder |
| 5,112,356 A | 5/1992 | Harris et al. |
| 5,116,384 A | 5/1992 | Wilson et al. |
| 5,139,525 A | 8/1992 | Kristinsson |
| 5,156,631 A | 10/1992 | Merlette |
| 5,181,932 A | 1/1993 | Phillips |
| 5,181,933 A | 1/1993 | Phillips |
| 5,219,365 A | 6/1993 | Sabolich |
| 5,258,039 A | 11/1993 | Goh et al. |
| 5,376,141 A | 1/1994 | Phillips |
| 5,290,319 A | 3/1994 | Phillips |
| 5,376,133 A | 12/1994 | ramnas |
| 5,387,246 A | 2/1995 | Phillips |
| 5,443,527 A | 8/1995 | Wilson |
| 5,443,529 A | 8/1995 | Phillips |
| 5,509,938 A | 4/1996 | Phillips |
| 5,545,234 A | 8/1996 | Collier, Jr. |
| 5,571,210 A | 11/1996 | Lindh |
| 5,653,767 A | 8/1997 | Allen et al. |
| 5,701,686 A | 12/1997 | Berr et al. |
| 5,728,177 A | 3/1998 | Phillips |
| 5,800,589 A | 9/1998 | Phillips |
| 5,888,239 A | 3/1999 | Wellershaus et al. |
| 5,897,594 A | 4/1999 | Martin et al. |
| 5,899,944 A | 5/1999 | Phillips |
| 5,913,901 A | 6/1999 | Lacroix |
| 5,941,913 A | 8/1999 | Woolnough et al. |
| 5,957,981 A | 9/1999 | Gramnas |
| 5,993,488 A | 11/1999 | Phillips |
| 6,071,313 A | 6/2000 | Phillips |
| 6,099,572 A | 8/2000 | Mosler et al. |
| 6,129,766 A | 10/2000 | Johnson et al. |
| 6,165,227 A | 12/2000 | Phillips |
| 6,206,934 B1 | 3/2001 | Phillips |
| 6,241,776 B1 | 6/2001 | Christensen |
| 6,261,324 B1 | 7/2001 | Merlette |
| 6,280,479 B1 | 8/2001 | Phillips |
| 6,350,286 B1 | 2/2002 | Atkinson et al. |
| 6,387,134 B1 | 5/2002 | Parker et al. |
| 6,398,818 B1 | 6/2002 | Merlette et al. |
| 6,402,790 B1 | 6/2002 | Celebi |
| 6,443,993 B1 | 9/2002 | Koniuk |
| 6,443,995 B1 | 9/2002 | Townsend et al. |
| 6,562,075 B2 | 5/2003 | Townsend et al. |
| 6,596,029 B1 | 7/2003 | Gramnas |
| 6,663,673 B2 | 12/2003 | Christensen |
| 6,712,860 B2 | 3/2004 | Rubie et al. |
| 6,719,807 B2 | 4/2004 | Harris |
| 6,767,370 B1 | 7/2004 | Mosier et al. |
| 6,793,683 B1 | 9/2004 | Laghi |
| 6,855,170 B2 | 2/2005 | Gramnas |
| 6,899,737 B1 | 5/2005 | Phillips |
| 6,942,704 B2 | 9/2005 | Sulprizio |
| 6,969,408 B2 | 11/2005 | Lecomte |
| 7,029,500 B2 | 4/2006 | Martin |
| 7,052,519 B1 | 5/2006 | Gramnas |
| 7,341,603 B2 | 3/2008 | Christensen |
| 7,347,877 B2 | 3/2008 | Clausen et al. |
| 7,507,259 B2 | 3/2009 | Townsend et al. |
| 7,520,904 B2 | 4/2009 | Christensen |
| 7,578,852 B2 | 8/2009 | Townsend et al. |
| 7,727,285 B2 | 6/2010 | Christensen et al. |
| 7,763,082 B1 | 7/2010 | Curtis |
| 7,766,974 B2 | 8/2010 | Curtis |
| 7,862,622 B2 | 1/2011 | Dunlap et al. |
| 7,942,935 B2 | 5/2011 | Iversen et al. |
| 8,007,544 B2 | 8/2011 | Jonsson et al. |
| 8,025,699 B2 | 9/2011 | Lecomte et al. |
| 8,246,695 B2 | 8/2012 | Mosler |
| 8,317,876 B2 | 11/2012 | Mosler |
| 8,377,144 B2 | 2/2013 | Jonsson et al. |
| 8,574,313 B2 | 11/2013 | Clausen et al. |
| 8,764,850 B2 | 7/2014 | Hanset et al. |
| 8,814,949 B2 | 8/2014 | Gramnaes |
| 8,888,864 B2 | 11/2014 | Iversen et al. |
| 8,915,969 B2 | 12/2014 | Boender |
| 9,366,306 B2 | 6/2016 | Miyasato et al. |
| 9,427,338 B2 | 8/2016 | Clausen et al. |
| 10,821,007 B2 | 11/2020 | Albertsson et al. |
| 10,980,648 B1 | 4/2021 | Lecomte et al. |
| 2002/0013628 A1 | 1/2002 | Harris |
| 2002/0040249 A1 | 4/2002 | Phillips |
| 2002/0087216 A1 | 7/2002 | Atkinson et al. |
| 2002/0116072 A1 | 8/2002 | Rubie et al. |
| 2002/0143408 A1 | 10/2002 | Townsend et al. |
| 2002/0183860 A1 | 12/2002 | Wilkinson |
| 2003/0093158 A1 | 5/2003 | Phillips |
| 2003/0120353 A1 | 6/2003 | Christensen |
| 2004/0064195 A1 | 4/2004 | Herr |
| 2004/0068327 A1 | 4/2004 | Christensen |
| 2004/0122529 A1 | 6/2004 | Townsend et al. |
| 2004/0162623 A1 | 8/2004 | Phillips |
| 2004/0181289 A1 | 9/2004 | Bedard et al. |
| 2004/0225376 A1 | 11/2004 | Townsend et al. |
| 2005/0038524 A1 | 2/2005 | Jonsson et al. |
| 2005/0038525 A1 | 2/2005 | Doddroe et al. |

(56) References Cited

U.S. PATENT DOCUMENTS

| | | | |
|---|---|---|---|
| 2005/0071018 A1* | 3/2005 | Phillips | A61F 2/66 623/55 |
| 2005/0107889 A1 | 5/2005 | Bedard et al. | |
| 2005/0137717 A1 | 6/2005 | Gramnas et al. | |
| 2005/0203640 A1* | 9/2005 | Christensen | A61F 2/66 623/55 |
| 2005/0267603 A1 | 12/2005 | Lecomte et al. | |
| 2005/0273179 A1 | 12/2005 | Townsend et al. | |
| 2006/0069450 A1 | 3/2006 | McCarvill et al. | |
| 2006/0235545 A1 | 10/2006 | Habecker | |
| 2007/0027557 A1 | 2/2007 | Jonsson et al. | |
| 2007/0250178 A1 | 10/2007 | Wilson | |
| 2008/0306612 A1* | 12/2008 | Mosier | A61F 2/66 623/53 |
| 2009/0204229 A1 | 8/2009 | Mosley et al. | |
| 2009/0222105 A1 | 9/2009 | Clausen | |
| 2012/0303135 A1* | 11/2012 | Vo | A61F 2/60 623/53 |
| 2013/0218297 A1 | 8/2013 | Nordman, Jr. et al. | |
| 2014/0249652 A1 | 9/2014 | Taszreak | |
| 2015/0257902 A1 | 9/2015 | Martin | |
| 2015/0328020 A1* | 11/2015 | Clausen | A61F 2/6607 623/25 |
| 2015/0351938 A1 | 12/2015 | Moser et al. | |
| 2016/0008147 A1 | 1/2016 | Marlin | |
| 2016/0033053 A1 | 2/2016 | Battlogg et al. | |
| 2016/0310298 A1 | 10/2016 | Johnson et al. | |
| 2017/0049584 A1 | 2/2017 | Pusch et al. | |
| 2017/0051808 A1 | 2/2017 | Bogrash et al. | |
| 2017/0128236 A1 | 5/2017 | Meyer et al. | |
| 2022/0062009 A1 | 3/2022 | Lecomte | |

FOREIGN PATENT DOCUMENTS

| | | | |
|---|---|---|---|
| DE | 817186 | 10/1951 | |
| DE | 834884 | 3/1952 | |
| DE | 838480 | 5/1952 | |
| DE | 924230 | 2/1955 | |
| DE | 832473 | 2/1957 | |
| DE | 1491182 | 7/1969 | |
| DE | 1941762 | 3/1971 | |
| DE | 22 41 971 | 3/1974 | |
| DE | 298 20 904 | 4/1999 | |
| DE | 200 15 175 | 12/2000 | |
| DE | 299 12 832 | 12/2000 | |
| DE | 200 19 178 U1 * | 2/2002 | A61F 2/6607 |
| EP | 0 401 864 A1 | 9/1989 | |
| EP | 0 940 129 A1 | 11/1992 | |
| EP | 1 149 568 A1 | 10/2001 | |
| EP | 0 648 479 A1 | 11/2015 | |
| EP | 2 944 290 A1 | 11/2015 | |
| FR | 661071 | 7/1929 | |
| FR | 1 169 280 * | 12/1958 | A61F 2/66 |
| FR | 1213026 | 3/1960 | |
| FR | 2658717 | 8/1991 | |
| GB | 117547 | 8/1918 | |
| GB | 120462 | 11/1918 | |
| GB | 621576 | 4/1949 | |
| GB | 625528 | 6/1949 | |
| GB | 1371996 | 10/1974 | |
| KR | 2000-0000930 | 1/2000 | |
| KR | 2000-0002059 | 1/2000 | |
| KR | 2000-0047310 | 7/2000 | |
| KR | 2001-0055393 | 7/2001 | |
| KR | 2002-0041137 | 6/2002 | |
| SE | 9400380-3 | 8/1995 | |
| SU | 1454449 A1 | 1/1989 | |
| SU | 1600759 A1 | 10/1990 | |
| SU | 1700759 A1 | 12/1991 | |
| WO | WO 88/06431 | 9/1988 | |
| WO | WO 93/04645 | 3/1993 | |
| WO | WO 94/10942 A1 * | 5/1994 | A61F 2/66 |
| WO | WO 94/18914 | 9/1994 | |
| WO | WO 96/04869 | 2/1996 | |
| WO | WO 98/53769 | 12/1998 | |
| WO | WO 99/52476 | 10/1999 | |
| WO | WO 00/27317 | 5/2000 | |
| WO | WO 01/06965 | 2/2001 | |
| WO | WO 02/02034 A1 | 1/2002 | |
| WO | WO 02/051342 | 7/2002 | |
| WO | WO 04/032809 | 4/2004 | |
| WO | WO 05/048887 | 6/2005 | |
| WO | WO 2011/066354 A2 | 6/2011 | |
| WO | WO 2017/077541 | 5/2017 | |

OTHER PUBLICATIONS

Commercial Ad for College Park Venture Prosthetic Foot; http://www.college-park.com/assets/pdf/VentureInfoSheets.pdf, © 2003, and www.college-park.com/CPStore/ProductInfoVenture.asp; available before Dec. 18, 2003.

Freedom Innovation Runway product; http://www.freedom-innovations.com/product_details.asp?seriesid=2&prodid=11, © 2004; available before Dec. 18, 2003.

Freedom Innovations FS2000 LP product; http://freedom-innovations.com/product_details.asp?seriesid=1&prodid=2, © 2003; available before Dec. 18, 2003.

International Search Report dated Apr. 28, 2006 for PCT/US2005/017884 filed May 20, 2005.

International Search Report dated May 27, 2005 for PCT/US2004/025554 filed Jun. 8, 2004.

Ohio Willow Wood Company: Carbon Copy System III brochure, 5 pages; believed to have been available prior to May 2004.

Össur Allurion product; http://www.ossur.com/template1.asp?pageid=84 and product catalog pp. 146-149; available before Dec. 18, 2003.

Össur Elation product; http://www.ossur.com/template1.asp?pageid=263 and product catalog pp. 193-196; available before Dec. 18, 2003.

Össur Total Concept product, Össur Products Catalog 2001-2002, pp. 243-249.

Otto Bock—Axtion product; http://www.ottobockus.com/products/lower_limb_prosthetics/axtion.asp; believed to have been released May 2004.

Invitation to Pay Additional Fees in corresponding International Patent Application No. PCT/US2017/064066, mailed Mar. 21, 2018, in 11 pages.

International Search Report and Written Opinion in corresponding International Patent Application No. PCT/US2017/064066, dated May 24, 2018, in 18 pages.

International Preliminary Report on Patentability and Written Opinion in PCT Application No. PCT/US2017/064066, dated Jun. 13, 2019.

Merlette et al., "The Springlite Foot, The Design Process for a Novel Advanced Composite Prosthesis", Composites In Manufacturing: Case Studies, Society of Manufacturing Engineers, 1991, pp. 269-288.

The Quantum Foot (Hosmer Dorrance Corporation), believed to be publicly available in or around 1998/1999.

The Quantum Foot brochure, believed to be publicly available in or around 1998/1999, 6 pages.

* cited by examiner

PROSTHETIC FEET HAVING HEEL HEIGHT ADJUSTABILITY

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57. This application is a continuation of U.S. patent application Ser. No. 15/828,944, filed Dec. 1, 2017, now U.S. Pat. No. 10,821,007, which claims priority benefit of U.S. Provisional Application No. 62/428,942, filed Dec. 1, 2016, the entirety of which is hereby incorporated by reference herein.

BACKGROUND

Field

The present application relates to foot prostheses in general, and more particularly, to prosthetic feet and ankles configured to allow for heel height adjustability.

Description of the Related Art

Various types of prosthetic foot and ankle devices are available as substitutes for human feet. Some prosthetic foot devices allow for heel height adjustment, for example, so that the user can wear shoes having different heel heights. However, in some cases, modifying the heel height alone without adjusting other sections of the prosthetic foot (e.g., the toe region) can place the foot in an unnatural position, which can result in discomfort for the user or a sub-optimal rollover performance during use. Additionally, some prosthetic foot devices allow for heel height adjustment at the ankle, but do not provide a mechanism for locking the ankle at a particular heel height. This can have an adverse effect on stability and/or performance of the foot in use.

SUMMARY

In some embodiments a prosthetic foot includes an ankle module, an elongate foot member, and an elongate lower foot member. The ankle module is configured to be coupled to a lower limb member. The elongate foot member extends from a proximal end to a distal end, and the proximal end is coupled to the ankle module. The elongate lower foot member extends from a proximal end to a distal end, is positioned below and coupled to the foot member, and extends distally beyond the distal end of the foot member to form a toe region. The ankle module is selectively actuatable to adjust an angle between the prosthetic foot and the lower limb member to allow for adjustment of a heel height of the prosthetic foot. The toe region curves upward and is configured to adapt to various heel heights of the prosthetic foot.

In some embodiments, the ankle module comprises a hydraulic adjustment mechanism. In some embodiments, the toe region comprises glass fiber. In some embodiments, the lower foot member comprises one or more layers of glass fiber extending from the proximal end to the distal end and one or more layers of carbon fiber extending from the proximal end to a point proximal of the distal end. The prosthetic foot can further include an upper foot member extending from a proximal end to a distal end, the upper foot member positioned above the foot member and the proximal end coupled to the proximal end of the foot member and the ankle module. The distal end of the upper foot member can be separated from the foot member by a gap when the prosthetic foot is at rest in a neutral position. The toe region can include a generally U-shaped cut-out extending proximally from the distal end of the lower foot member, the lower foot member can include a split extending at least partially along a longitudinal axis of the lower foot member to the cut-out, and a transition between the split and the cut-out can be rounded. The prosthetic foot can include a toe piece coupled to a top surface of the toe region. The toe piece can taper toward a front or distal end of the toe piece.

In some embodiments, a prosthetic foot includes an elongate foot member, an elongate lower foot member, and an ankle module. The elongate foot member extends from a proximal end to a distal end. The elongate lower foot member extends from a proximal end to a distal end, is positioned below and coupled to the foot member, and extends distally beyond the distal end of the foot member to form a toe region. The ankle module is coupled to the proximal end of the foot member and configured to be coupled to a lower limb member. The ankle module includes first and second pistons, a central cavity between the first and second pistons, a hydraulic fluid in the central cavity, an intermediate wall separating the central cavity into first and second cylinders, a spool valve extending through the intermediate wall, the spool valve actuatable to selectively place the first and second cylinders in fluid communication, and a ball lock actuatable to selectively place the valve in an open or closed position, the ball lock comprising a first end portion or button, one or more balls, and at least one spring. The ankle module is selectively actuatable to adjust an angle between the prosthetic foot and the lower limb member to allow for adjustment of a heel height of the prosthetic foot. The ball lock can include a second end portion disposed opposite the first end portion along the spool valve, at least one button spring, and a wire attached to the second end portion. When a user pulls the wire in use, the wire can cause movement of the second end portion, thereby shifting the spool valve to the open position and compressing the at least one button spring. The ball lock can include a secondary wire attached to the first end portion. When a user pulls the secondary wire in use, the secondary wire can cause movement of the first end portion, thereby shifting the spool valve to the closed position. The ankle module can include a washer coupled to a lower surface of at least one of the first and second pistons and a piston base coupled to a base portion of the ankle module. The washer can have a downward-facing convex bottom surface, and the piston base can have an upward-facing concave upper surface configured to pivotably receive the downward-facing convex bottom surface of the washer to accommodate changes in an angle between the at least one of the first and second pistons and the base portion.

In some embodiments, the toe region curves upward and is configured to adapt to various heel heights of the prosthetic foot. In some embodiments, the toe region comprises glass fiber. In some embodiments, the lower foot member comprises one or more layers of glass fiber extending from the proximal end to the distal end and one or more layers of carbon fiber extending from the proximal end to a point proximal of the distal end. The prosthetic foot can further include an upper foot member extending from a proximal end to a distal end, the upper foot member positioned above the foot member and the proximal end coupled to the proximal end of the foot member and the ankle module. The distal end of the upper foot member can be separated from the foot member by a gap when the prosthetic foot is at rest in a neutral position.

In some embodiments, a prosthetic foot includes an elongate foot member, an ankle module, and a cosmesis. The elongate foot extends from a proximal end to a distal end and has an arch region therebetween. The ankle module is operably coupled to the foot member and configured to be coupled to a lower limb member. The ankle module is selectively actuatable to adjust an angle between the prosthetic foot and the lower limb member to allow for adjustment of a heel height of the prosthetic foot. The cosmesis is configured to receive the foot member. When the foot member is disposed in the cosmesis and the foot is resting on a support surface in a neutral position with the prosthetic foot adjusted to a neutral heel height, the arch region of the foot member is separated from an inner surface of a sole portion of the cosmesis by a gap. The gap can allow the cosmesis to adapt to varying heel heights of the prosthetic foot.

In some embodiments, the foot member includes a toe region adjacent the distal end. The toe region can curve upward and be configured to adapt to various heel heights of the prosthetic foot. The toe region can include a glass fiber. In some embodiments, the foot member comprises one or more layers of glass fiber extending from the proximal end to the distal end and one or more layers of carbon fiber extending from the proximal end to a point proximal of the distal end. A toe piece can be coupled to a top surface of the toe region to at least partially fill a gap between the toe region and an inner surface of the cosmesis.

In some embodiments, a cosmesis for a prosthetic foot member includes an outer wall defining an inner cavity, the inner cavity is configured to receive the prosthetic foot, and a heel end of the outer wall is vertically offset from a toe end of the outer wall by a distance in the range of about 2 cm to about 4 cm.

In some embodiments, a cosmesis for a prosthetic foot includes a foot portion and a calf portion. The foot portion includes an opening at a top end extending into a cavity formed within the foot portion, the cavity configured to removably receive the prosthetic foot therein, and a wall surrounding the cavity. A lower end of the calf portion can be configured to be coupled to the top end of the foot portion about the opening, and the foot portion can have a height such that the top end and opening are configured to be positioned below an opening of a shoe when the cosmesis is disposed in the shoe. In some embodiments, the foot portion includes a recess in an inner surface of the foot portion proximate the top end, and the calf portion includes a lip adjacent the lower end, and the recess is configured to receive the lip.

In some embodiments, a cosmesis for a prosthetic foot including an ankle module includes a foot portion and a calf portion. The foot portion includes an opening at a top end extending into a cavity formed within the foot portion, the cavity configured to removably receive the prosthetic foot therein, and a wall surrounding the cavity. The calf portion includes a wall surrounding a cavity, a lower end of the calf portion is configured to be coupled to the top end of the foot portion about the opening, and a portion of the wall of the calf portion configured to be positioned proximate an adjustment button of the ankle module when the prosthetic foot is disposed in the cosmesis has a thickness less than a thickness of a remainder of the wall of the calf portion. In some embodiments, the foot portion has a height such that the top end and opening are configured to be positioned below an opening of a shoe when the cosmesis is disposed in the shoe.

All of these embodiments are intended to be within the scope of the disclosure herein. These and other embodiments will become readily apparent to those skilled in the art from the following detailed description having reference to the attached figures, the disclosure not being limited to any particular disclosed embodiment(s).

BRIEF DESCRIPTION OF THE DRAWINGS

These and other features, aspects, and advantages of the present disclosure are described with reference to the drawings of certain embodiments, which are intended to schematically illustrate certain embodiments and not to limit the disclosure.

DETAILED DESCRIPTION

Although certain embodiments and examples are described below, those of skill in the art will appreciate that the disclosure extends beyond the specifically disclosed embodiments and/or uses and obvious modifications and equivalents thereof. Thus, it is intended that the scope of the disclosure herein disclosed should not be limited by any particular embodiments described below.

Figure 1:
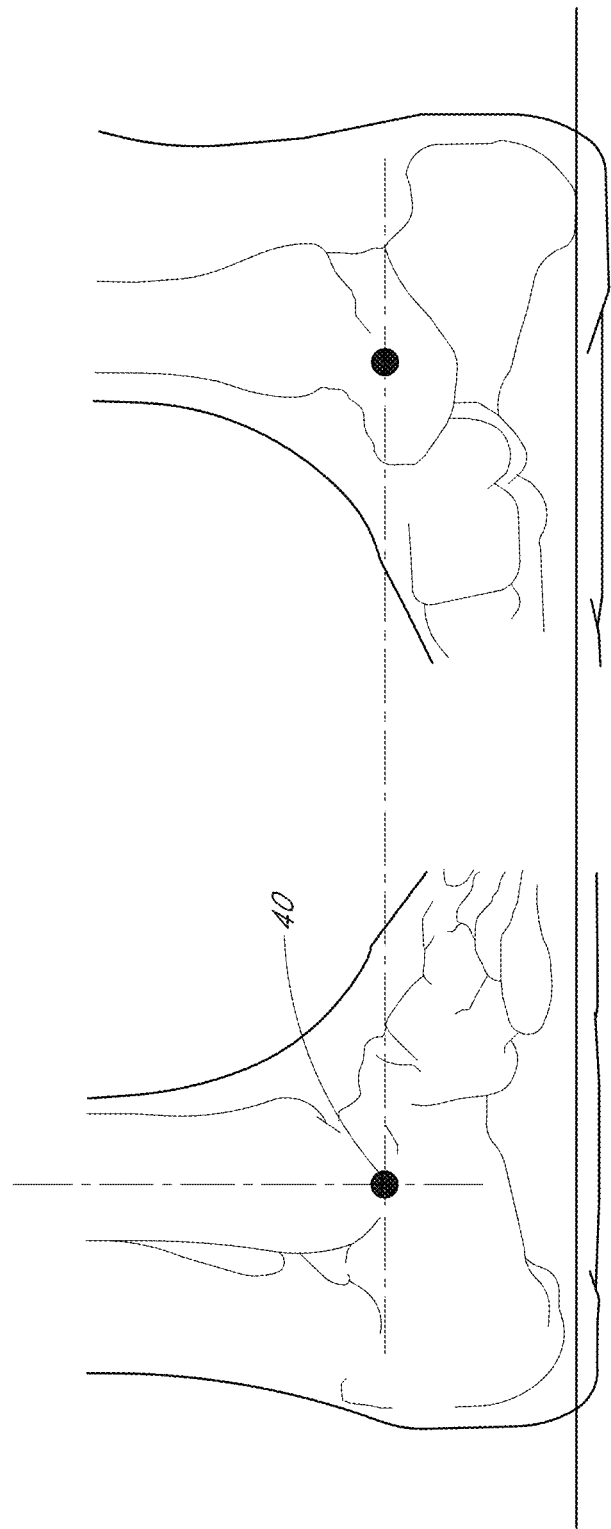
FIG. 1 illustrates a schematic of a natural human ankle joint.
Figure 2:
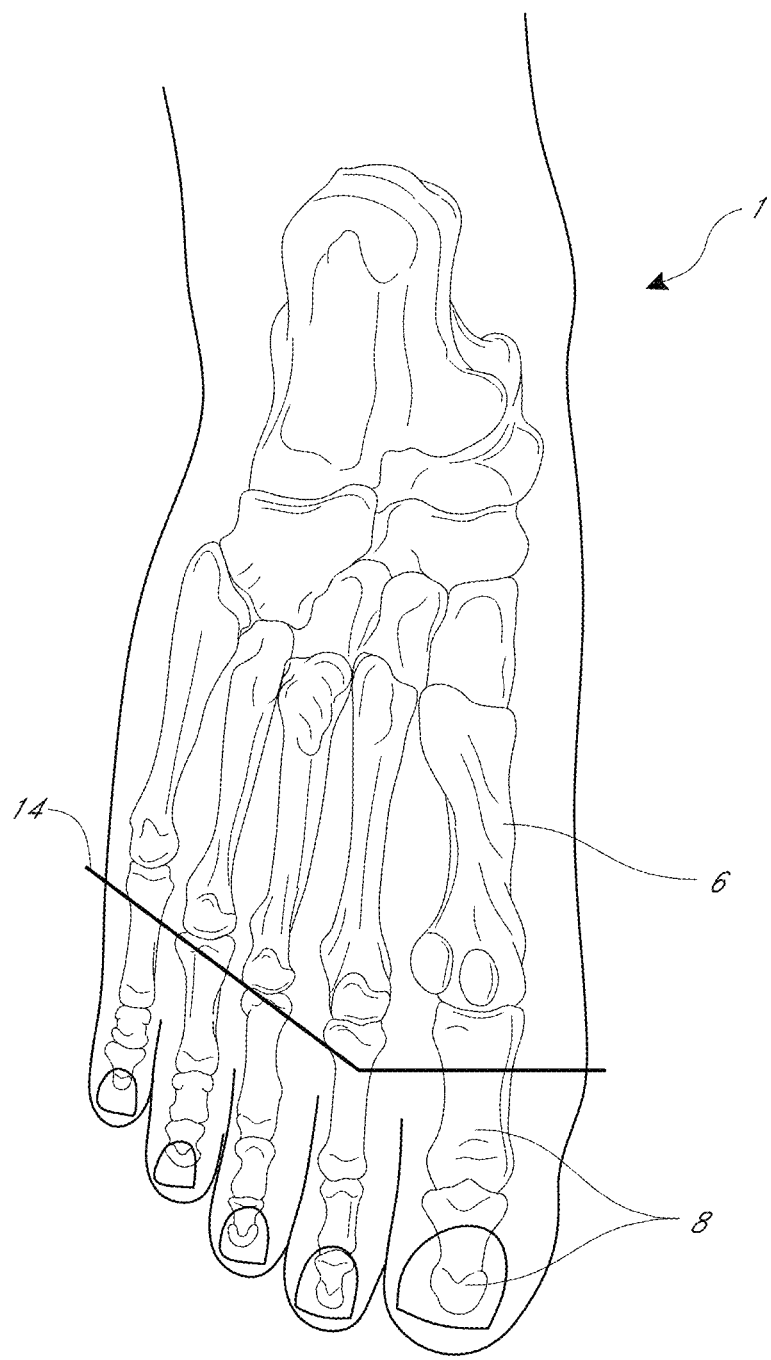
FIG. 2 illustrates a schematic of bones and joints of a natural human foot.

A natural human ankle allows for changes in an angle between the lower leg and the foot. This allows the foot and ankle to, among other things, adapt to shoes having different heel heights. For example, a natural human ankle can allow for angular adjustment about a pivot point at the ankle joint 40, as shown in FIG. 1. A natural human foot 1 also includes metatarsal joints between the metatarsal bones 6 and the phalanges 8 that form the toes, as shown in FIG. 2. These joints allow the phalanges 8 to articulate relative to the metatarsal bones 6, such as at the natural metatarsal angles 14. This allows the posterior or heel of the foot to be angled relative to the forefoot or toes of the foot and allows the foot to further adapt to shoes having varying heel heights while providing support and balance.

Some prosthetic feet currently available have a fixed ankle angle or are adapted primarily for use at a single heel height. Prosthetic feet according to the present disclosure advantageously allow for heel height adjustment and/or allow the toe to adapt to various heel heights to more closely mimic natural human feet (e.g., more closely approximate the functionality provided by the ankle and metatarsal joints of natural human feet).

A prosthetic foot as described herein can generally include an adjustment and locking mechanism configured to lock the heel at a particular height (e.g., by locking an adapter of the foot at a particular angular orientation relative to a foot member of the foot) and/or a toe portion that allows the toe to adapt to various heel heights. In some embodiments, a prosthetic foot includes an ankle module that allows for heel height adjustment and includes at least a portion of the locking mechanism. The ankle module can include an adapter or connector to couple the ankle module and therefore the prosthetic foot to a prosthetic pylon or socket. The adjustment and/or locking mechanism can advantageously allow the ankle and/or foot to be adjusted and locked so that the connector remains vertical or at least substantially vertical at different heel heights. When changing to a shoe having a different heel height, the user can unlock the locking mechanism, adjust the foot (or allow the foot to adjust) to the correct height and alignment, then lock the locking mechanism. In some embodiments, the prosthetic foot can be disposed in a cosmesis that can include a foot portion and/or a calf portion.

Figure 3:
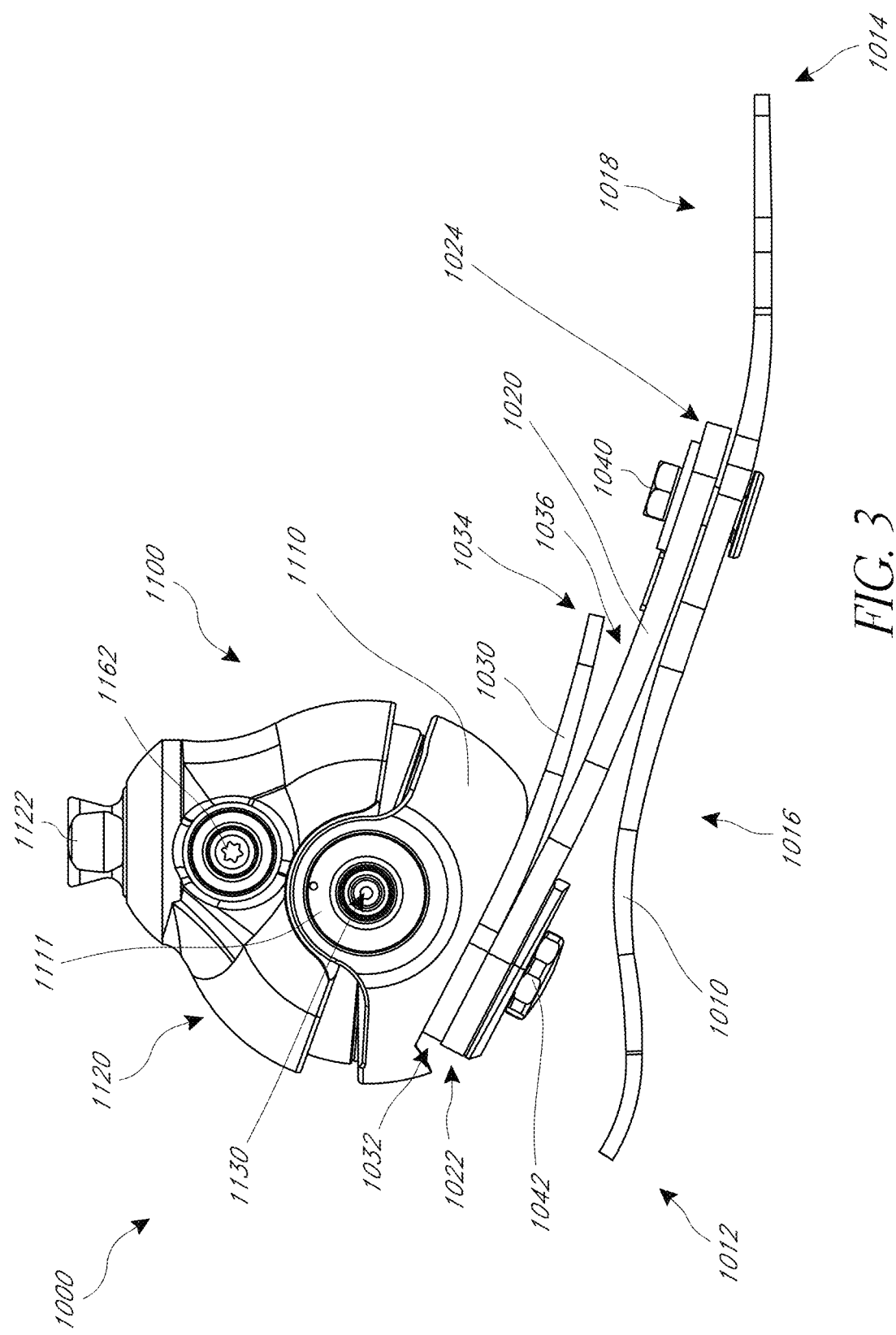
FIG. 3 illustrates an example embodiment of a prosthetic foot having heel height adjustability.

FIG. 3 illustrates one example embodiment of a prosthetic foot 1000 that allows for heel height adjustment. In the illustrated embodiment, the prosthetic foot 1000 includes a lower foot member 1010, an intermediate foot member 1020, and an upper foot member 1030. The lower foot member 1010 is substantially plate-like and has a generally rectangular or rectangular cross-section transverse to a longitudinal axis of the lower foot member 1010 along at least a portion of its length. The lower foot member 1010 extends from a proximal or heel end 1012 to a distal or toe end 1014 and includes an arch region 1016 between the heel end 1012 and the toe end 1014, for example, at approximately the location of an arch of a natural human foot.

The intermediate foot member 1020 is substantially plate-like and has a generally rectangular or rectangular cross-section transverse to the longitudinal axis along at least a portion of its length. The intermediate foot member 1020 extends from a proximal end 1022 downward and forward to a distal end 1024. As shown, the intermediate foot member 1020 is coupled to the lower member 1010 with one or more fasteners 1040, e.g., bolts, positioned proximate the distal end 1024 of the intermediate foot member 1020, and the lower foot member 1010 extends beyond or distal to the distal end 1024 of the intermediate foot member 1020. In the illustrated embodiment, the distal end 1024 of the intermediate foot member 1020 and fasteners 1040 are positioned adjacent and distal to the arch region 1016 (e.g., proximate a portion of the foot 1000 generally corresponding to a metatarsal region of a natural human foot). In some embodiments, the intermediate foot member 1020 tapers (e.g., gradually tapers) toward the proximal end 1022 such that the distal end 1024 of the intermediate foot member 1020 is thicker than the proximal end 1022.

The upper foot member 1030 extends from a proximal end 1032 to a distal end 1034. As shown, the proximal end 1032 of the upper foot member 1030 can be coupled to the proximal end 1022 of the intermediate foot member 1020, for example, via one or more fasteners 1042 such as bolts. In the illustrated embodiment, there is a gap 1036 between the distal end 1034 of the upper foot member 1030 and a top surface of the intermediate foot member 1020. During the mid-stance and toe-off phases of the gait cycle, the gap 1036 can close and the upper foot member 1030 can engage the intermediate foot member 1020 to increase the stiffness of the foot 100 and/or store additional energy in the intermediate foot member 1020 as the foot 100 moves toward toe-off. In some embodiments, the upper foot member 1030 is tapered (e.g., gradually tapered) toward the distal end 1034 such that the distal end 1034 is thinner than the proximal end 1032.

In some embodiments, the foot members or portions of the foot members can be constructed of a strong, resilient material that is capable of flexing in multiple directions, particularly during heel-strike through toe-off. The material can comprise multiple layers, or laminate. In some embodiments, the multiple layers or laminates when assembled form a monolithic member. Examples of possible materials for portion of the prosthetic foot include carbon, a polymer material, and a composite of polymer and fiber. The polymer can be thermoset or thermoplastic. In a composite, the fiber reinforcement can be any type of fiber or filament, such as carbon, glass or aramid. The fibers can be long and unidirectional, or they can be chopped and randomly oriented. Other filaments, such as Kevlar and nylon, can also be used to ensure lightweight and structurally dynamic characteristics. Additional details regarding the lower 1010, intermediate 1020, and/or upper 1030 foot members can be found in U.S. Publication No. 2016/0310298, the entirety of which is hereby incorporated by reference herein.

Other arrangements of foot members are also possible. For example, in some embodiments, the intermediate foot member 1020 extends from the proximal end 1022 to a toe end, and the lower foot member 1010 is a heel plate that extends from a heel end to a distal end and includes an arch region between the heel end and the distal end. The heel plate is coupled to the intermediate foot member 1022 proximal to the toe end of the intermediate foot member 1020 and proximate to the distal end of the lower foot member 1010. In some such embodiments, the intermediate foot member 1022 tapers (e.g., gradually tapers) toward both the proximal end and distal toe end such that the intermediate foot member is thicker in a region where fasteners couple the intermediate foot member 1020 to the lower foot member 1010. In some embodiments, the prosthetic foot 1000 does not include an upper foot member 1030.

In the illustrated embodiment, the prosthetic foot 1000 includes an ankle module 1100 placed adjacent and coupled to a top surface of the upper foot member 1030 at, adjacent, or proximate the proximal end 1032. As shown, the ankle module 1100 can also be coupled indirectly to the intermediate foot member 1020 because the proximal end 1022 of the intermediate foot member 1020 is coupled to the proximal end 1032 of the upper foot member 1030. In embodiments not including an upper foot member 1030, the ankle module 1100 can be placed adjacent and coupled to the top surface of the intermediate foot member 1020 at, adjacent, or proximate the proximal end 1022.

Ankle Adjustment and Locking Mechanism

Figure 4:
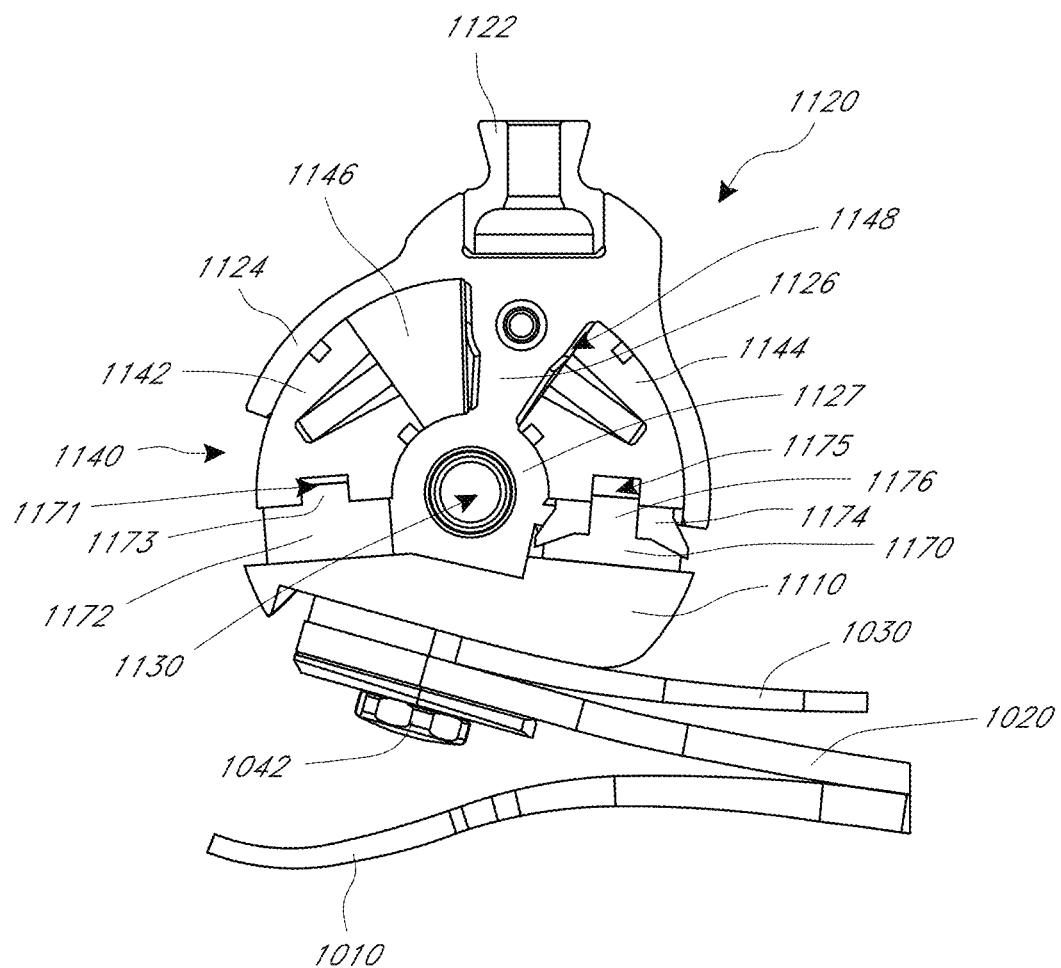
FIG. 4 illustrates a longitudinal cross-sectional view of an ankle module of the prosthetic foot of FIG. 3.

The ankle module 1100 of the embodiment illustrated in FIG. 3 includes a hydraulic adjustment and locking mechanism. As shown in FIGS. 3-4, the ankle module 1100 includes a base portion 1110 and an adapter portion 1120. The base portion 1110 is coupled (e.g., fixedly coupled in the illustrated embodiment) to a foot member of the prosthetic foot 1000. In the illustrated embodiment, the base portion 1110 is coupled to the upper foot member 1030 at, adjacent, or proximate the proximal end 1032. In embodiments not including the upper foot member 1030, the base portion 1110 can be coupled to the intermediate foot member 1020 at, adjacent, or proximate the proximal end 1022. The base portion 1110 can be coupled to the upper foot member 1030 and/or intermediate foot member 1020 with one or more fasteners 1042 as shown. The adapter portion 1120 includes a connector or adapter 1122 that is coupled (e.g., fixedly coupled in the illustrated embodiment) to the user's residual limb via a socket or another prosthetic component, such as a pylon, in use. In the illustrated embodiment, the adapter 1122 is a male pyramid.

The adapter portion 1120 and base portion 1110 are pivotably or rotatably coupled via a pivot point or axle 1130 extending medially-laterally through the ankle module 1100. The adapter portion 1120 and base portion 1110 can be pivoted or rotated relative to each other in a dorsi-plantar direction to adjust an angle between the user's lower leg (e.g., the residual limb or pylon) and the prosthetic foot and therefore the heel height of the prosthetic foot. The axle 1130 can be fixedly coupled to the base portion 1110, and the adapter portion 1120 can be pivotably or rotatably coupled to the axle 1130. In other embodiments, the axle 1130 can be fixedly coupled to the adapter portion 1120 and pivotably or rotatably coupled to the base portion 1110. In the illustrated embodiment, the base portion 1110 includes projections or shoulders 1111 extending upward from medial and lateral sides of the base portion 1110 beyond a lower edge of the adapter portion 1120 (e.g., a lower edge of an outer housing 1124 of the adapter portion 1120, described below). The axle 1130 can extend through and be coupled (e.g. fixedly, pivotably, or rotatably) to the shoulders 1111.

As shown in FIG. 4, the adapter portion 1120 includes an outer housing 1124 and an intermediate wall 1126. The intermediate wall 1126 extends between an inner surface of the outer housing 1124 and a central hub 1127. The central hub 1127 encircles and can pivot or rotate about the axle 1130 that couples the adapter portion 1120 and base potion 1110. In the illustrated embodiment, the intermediate wall 1126 is integrally formed with the outer housing 1124 and the central hub 1127. In some embodiments, the intermediate wall 1126 can be separately formed from and coupled to the outer housing 1124 and/or the central hub 1127.

The ankle module 1100 further includes an inner body 1140 including a proximal or rear piston 1142, a distal or front piston 1144, and a central cavity between the front 1144 and rear 1142 pistons. The intermediate wall 1126 divides the central cavity into rear and forward cylinders 1146, 1148. The cylinders 1146, 1148 house or contain hydraulic fluid. In the illustrated embodiment, the outer housing 1124 and inner body 1140 have a generally semi-circular cross-section taken along a dorsi-plantar plane (as shown in FIG. 4).

Figure 5:
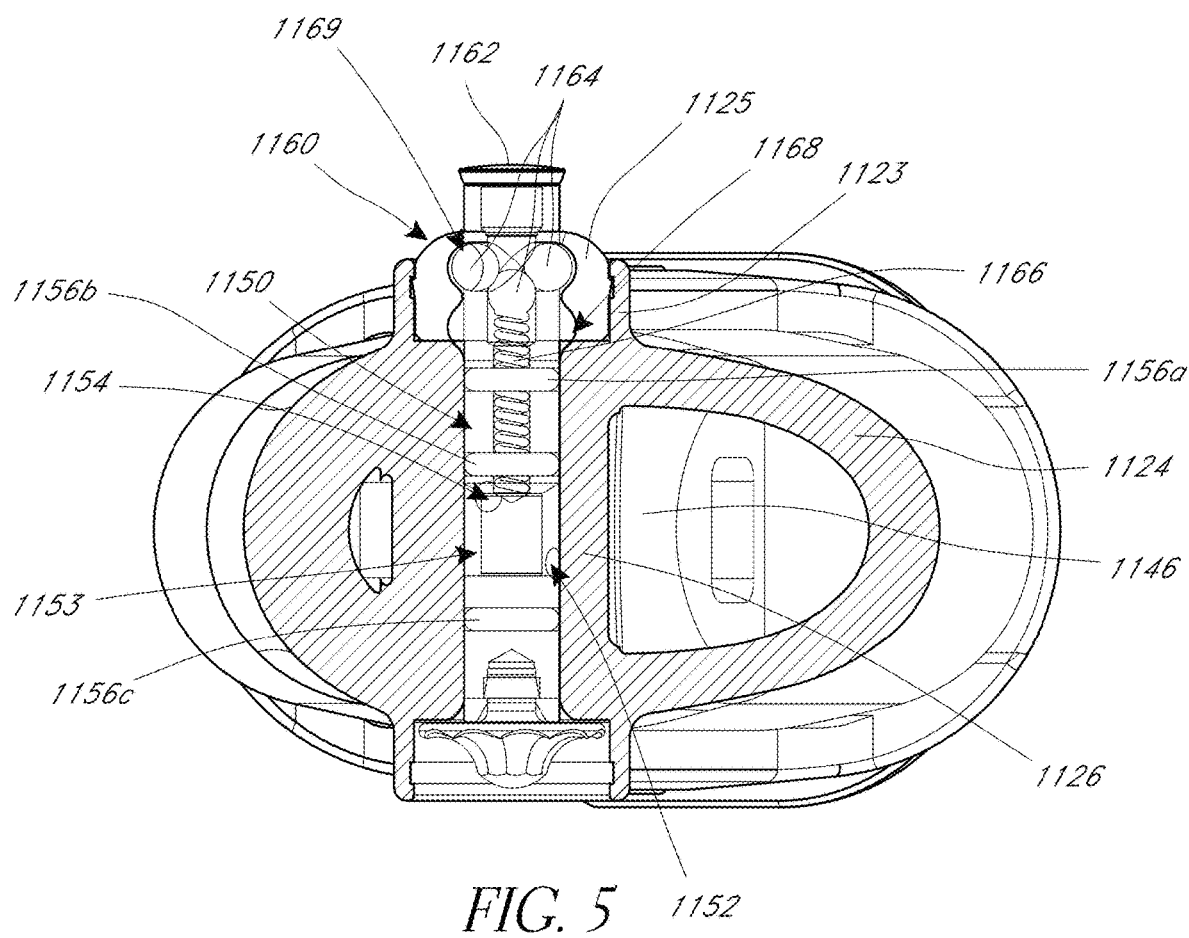
FIG. 5 illustrates a top sectional view of the ankle module of FIG. 4.

As shown in FIG. 5, the ankle module 1100 includes a spool valve 1150 extending medially-laterally through a bore in the adapter portion 1120. As shown, the bore and valve 1150 extend through the intermediate wall 1126, for example, an end of the intermediate wall 1126 proximate or adjacent the adapter 1122. A first hole 1152 extends through the intermediate wall 1126 from the rear cylinder 1146 to the bore and places the bore in fluid communication with the rear cylinder 1146. A second hole 1154 extends through the intermediate wall 1126 from the forward cylinder 1148 to the bore and places the bore in fluid communication with the forward cylinder 1148. The valve 1150 includes a reduced diameter portion 1153 having a length that allows the valve 1150 to be selectively positioned within the bore so that the first 1152 and second 1154 holes can fluidly communicate with each other via a gap between the reduced diameter portion 1153 and a surface of the bore. In the illustrated embodiment, the valve 1150 includes three sealing members (e.g., o-rings), a first sealing member 1156a, a second sealing member 1156b, and a third sealing member 1156c. The sealing members 1156a, 1156b, 1156c seal against the surface of the bore to prevent or inhibit the fluid from flowing medially or laterally out of the valve 1150 and leaking from the ankle module 1100. When the valve 1150 is an open position, as shown in FIG. 5, the sealing members 1156a, 1156b, 1156c are all positioned medially or laterally of both the first 1152 and second 1154 holes. In other words, none of the sealing members 1156a, 1156b, 1156c is positioned between the first 1152 and second 1154 holes. Fluid can therefore flow between the rear cylinder 1146 and forward cylinder 1148 through the first 1152 and second 1154 holes and reduced diameter portion 1153 of the valve 1150. When the valve 1150 is moved to a closed position, the second sealing member 1156b is positioned between the first hole 1152 and the second hole 1154. Fluid is therefore blocked, prevented, or inhibited from flowing between the cylinders 1146, 1148.

When the valve 1150 is in the open position, as fluid flows from the rear cylinder 1146 into the forward cylinder 1148, the central hub 1127 rotates about the axle 1130 and the intermediate wall 1126 moves rearward toward the rear piston 1142. Rearward movement of the intermediate wall 1126 increases the angle between the user's lower limb and the foot, thereby increasing the heel height. As fluid flows from the forward cylinder 1148 into the rear cylinder 1146, the central hub 1127 rotates about the axle 1130 and the intermediate wall 1126 moves forward toward the front piston 1144, thereby decreasing the angle between the lower limb and the foot and decreasing the heel height. The front piston 1144 and rear piston 1142 can at least partially define a range of motion or adjustment for the ankle module 1100.

Figure 18:
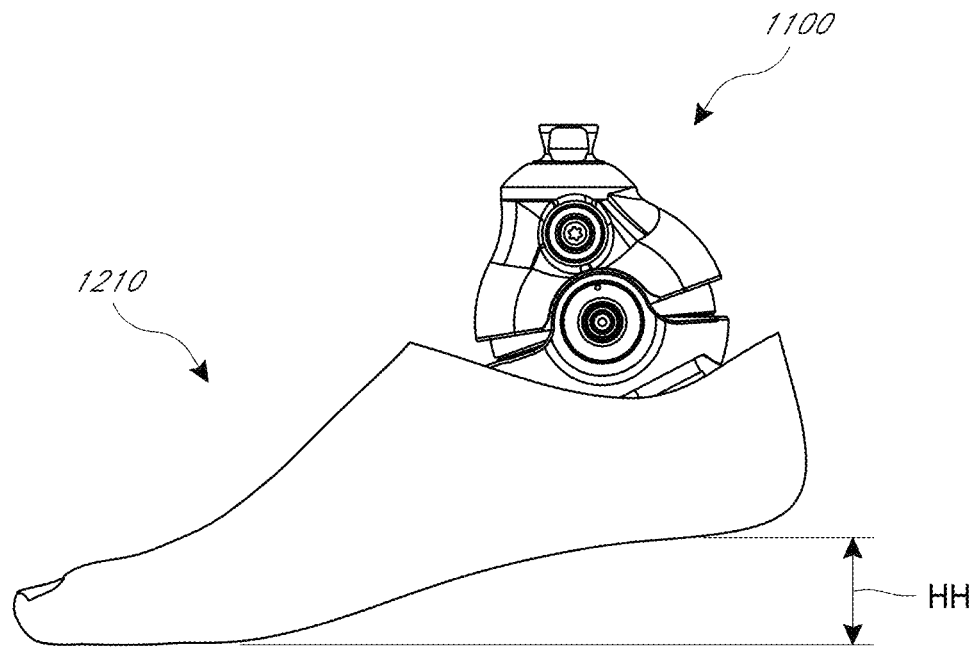
FIG. 18 illustrates the prosthetic foot and foot portion of the cosmesis of FIG. 8.

In some embodiments, the ankle module 1100 has a range of motion or adjustment of 7 cm or about 7 cm. In other words, the ankle module 1100 can adjust to heel heights over a range of 7 cm. The heel height can be defined as a distance between the ground or a support surface on which the user is standing in a neutral position and the heel end of the prosthetic foot (e.g., the proximal end 1012 of the lower foot member 1010) or the bottom surface of a heel portion of a cosmesis in which the prosthetic foot is received, for example as shown in FIG. 18, where HH indicates the heel height. In some embodiments, the ankle module 1100 may allow adjustment of the heel height of the prosthetic foot from a flat foot position, e.g., 0 cm, to a heel height of 7 cm. In some embodiments, a "flat foot" or neutral position of the prosthetic foot may have a heel height greater than 0 cm, e.g., 1 cm. In some such embodiments, the ankle module 1100 can allow adjustment of the heel height of the prosthetic foot from the flat foot position to a heel height of 7 cm greater than the flat foot heel height, for example, 8 cm in an embodiment in which the flat foot position has a heel height of 1 cm. In some embodiments, the flat foot or neutral position may have a heel height greater than 0 cm, and the ankle module 1100 can allow adjustment of the heel height between 0 cm and, for example, 7 cm. In some embodiments, the ankle module 1100 can have a range of motion or adjustment of greater than or less than 7 cm.

As shown in FIG. 4, the ankle module 1120 can include a front bumper 1170 and a rear bumper 1172. The front bumper 1170 is positioned proximate or adjacent the front piston 1144 (an end of the front piston 1144 opposite an end of the front piston 1144 that is adjacent the forward cylinder 1148). The front piston 1144 may contact the front bumper 1170 in use. The rear bumper 1172 is positioned proximate or adjacent the rear piston 1142 (an end of the rear piston 1142 opposite an end of the rear piston 1142 that is adjacent the rear cylinder 1146). The rear piston 1142 may contact the rear bumper 1172 in use. The front 1170 and rear 1172 bumpers can help minimize or reduce play in the ankle module 1100. In some embodiments, the front 1170 and rear 1172 bumpers can act as accumulators and store energy during use. In the illustrated embodiment, a stiff member 1174 is positioned between at least a portion of the front bumper 1170 and the front piston 1144. In the illustrated embodiment, the rear piston 1142 includes a recess 1171 to receive a corresponding protrusion 1173 of the rear bumper 1172. In the illustrated embodiment, the front piston 1144 includes a recess 1175 to receive a corresponding protrusion 1176 of the front bumper 1170.

Figure 6:
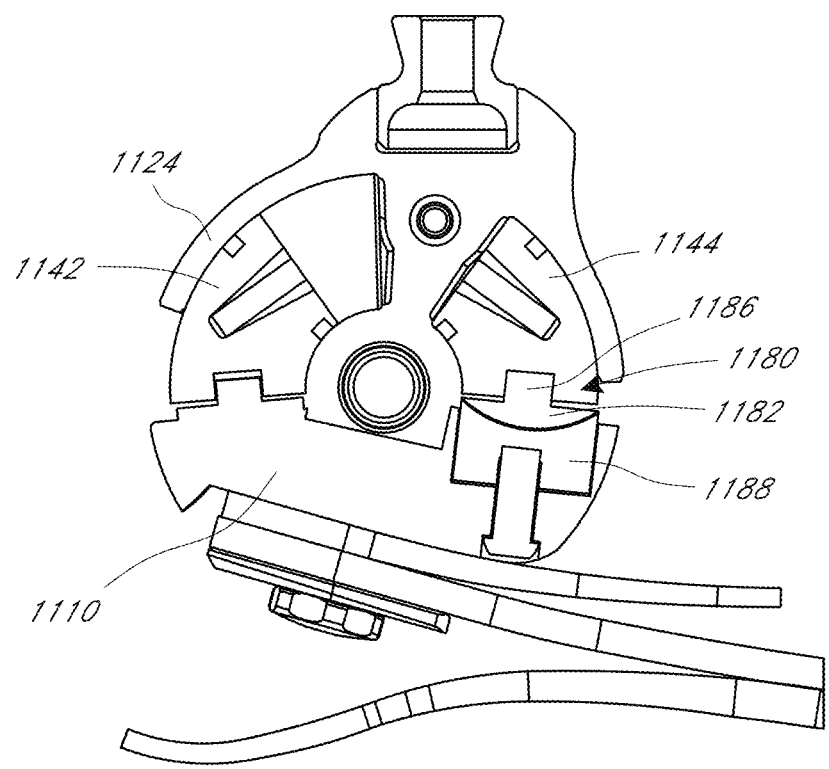
FIG. 6 illustrates a perspective longitudinal cross-sectional view of an example embodiment of an ankle module.
Figure 7A:
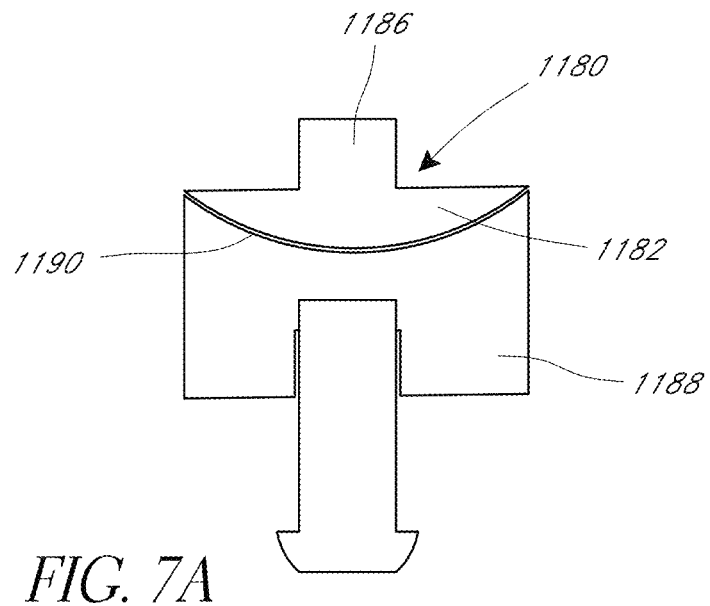
FIGS. 7A-7B illustrate schematics of a spherical washer of the ankle module of FIG. 6.
Figure 7B:
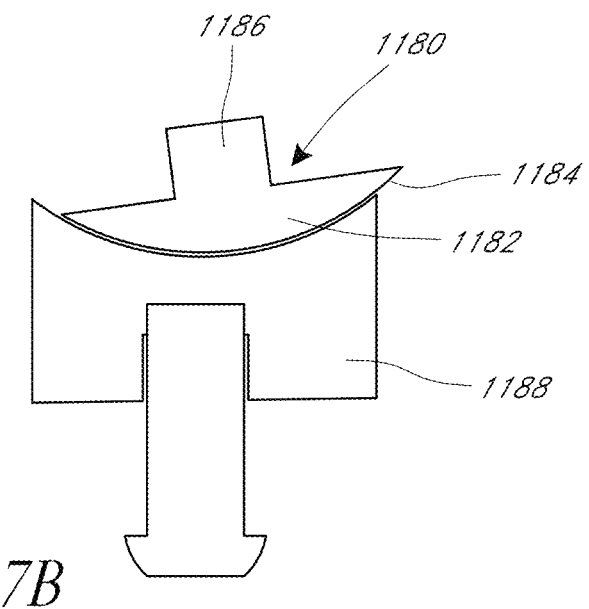

During assembly of the ankle module 1120, optionally, one or both of the pistons 1144, 1142 can be compressed to remove air from the hydraulic chambers. As the pistons 1144, 1142 are inserted during assembly, the angle of the lower surfaces of the pistons 1144, 1142 (i.e., the end surfaces of the pistons 1144, 1142 positioned toward or facing the base portion 1110) relative to the base portion 1110 may change. The bumpers 1172, 1170 can deform to accommodate such changes or tolerances. Instead of or in addition to the bumpers 1172, 1170, the ankle module 1120 can include one or more at least partially spherical washers 1180 as shown in FIGS. 6-7B. A washer 1180 can be coupled, e.g., fixedly coupled, to or relative to the lower surface of one or both of the pistons 1142, 1144. In the embodiment of FIG. 6, a washer 1180 is coupled to the front piston 1144. In the illustrated embodiment, the washer 1180 has a partial spherical portion 1182 having a downward-facing convex partially spherical bottom surface 1184 and a post 1186 extending upward from the partial spherical portion. The post 1186 is coupled to the piston 1144, 1142. A piston base 1188 is coupled, e.g., fixedly coupled, to the base portion 1110. The piston base 1188 has an upward-facing concave upper surface 1190 that receives and/or accommodates the downward-facing convex bottom surface 1184 of the washer 1180 as shown. The washer 1180 can pivot or rotate relative to the piston base 1188 to accommodate and adapt to changes in the angle between the piston 1144, 1142 and the base portion 1110.

In the illustrated embodiment, the ankle module 1100 includes a ball lock system 1160 that allows the spool valve 1150 to be adjusted to and/or locked in the open and/or closed position. The ball lock system 1160 is actuatable to slide within a channel in the ankle module 1100 to operate the spool valve 1150 between the open and locked positions. As shown, the ball lock system 1160 includes an end portion or button 1162, a plurality of balls 1164, and at least one spring 1166. The adapter portion 1120 and/or inner body 1140 includes recesses that receive the balls 1164. In the illustrated embodiment, a cap piece 1125 is coupled to and/or within a projection 1123 extending medially or laterally from the outer housing 1124. As shown, the adapter portion 1120, inner body 1140, and/or projection 1123 includes a first set of recesses 1168 positioned relatively more centrally that receive the balls 1164 when the valve 1150 is in the closed position. The adapter portion 1120, inner body 1140, and/or projection 1123 includes a second set of recesses 1169 positioned relatively more medially or laterally that receive the balls 1164 when the valve 1150 is in the open position. In use, the user presses the button 1162 to move the balls 1164 and the valve 1150 between the open and closed positions. The spring(s) 1166 spring loads the balls 1164, which advantageously provides the user with tactile feedback that the valve 1150 has been fully moved to the desired open or closed position. Such tactile feedback can be particularly useful when the prosthetic foot 1000 is disposed within a cosmesis, for example as described in greater detail herein, and the user is therefore depressing the button 1162 through the cosmesis.

Figure 8A:
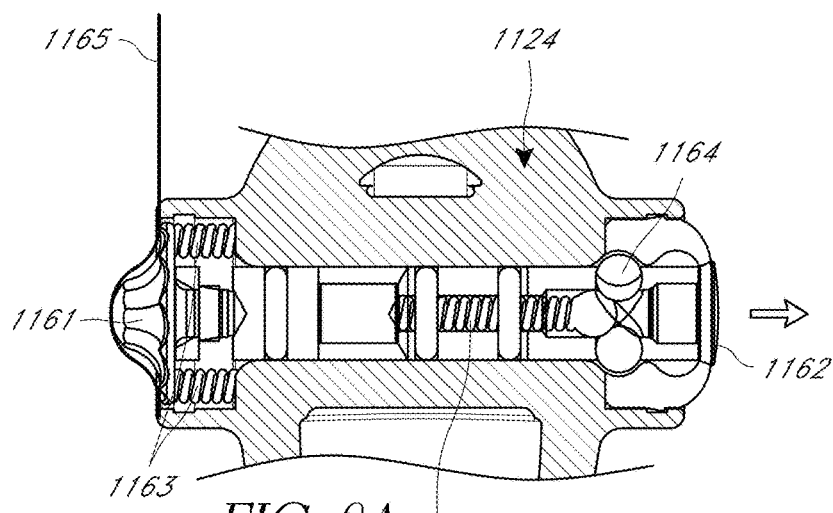
FIGS. 8A-8C illustrate schematic side cross-sectional views an example embodiment of an ankle module showing operation of a flow valve.
Figure 8B:
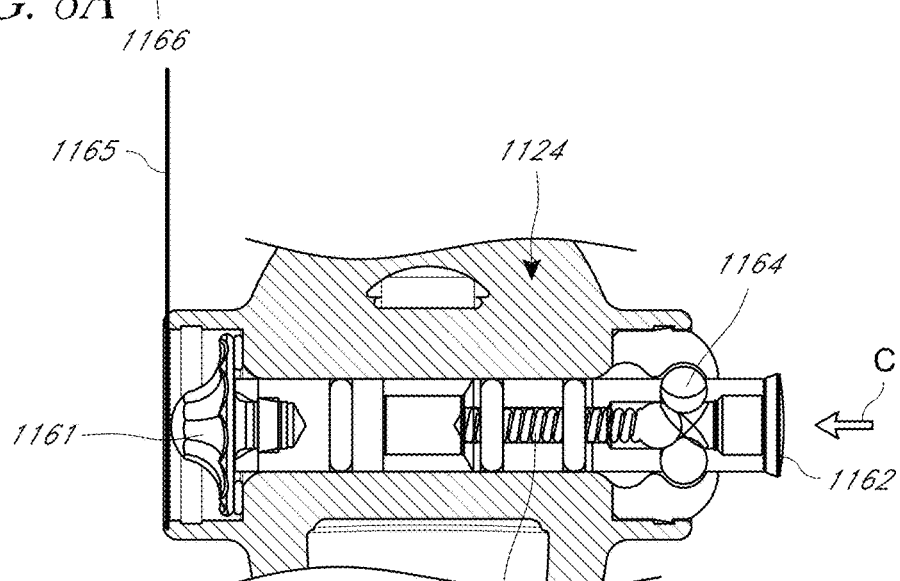
Figure 8C:
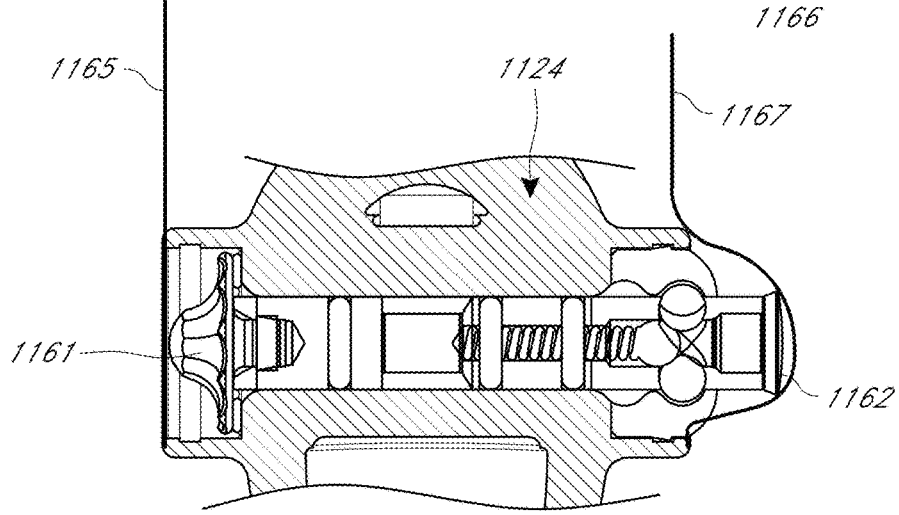

FIGS. 8A-8B illustrate an alternative system and method for opening and closing the spool valve 1150. As shown, the ankle module includes a ball lock system 1160 that extends through a channel in the ankle module. The ball lock system 1160 is actuatable to slide within the channel to operate the spool valve 1150 between the open and closed positions. In this embodiment, the ball lock system 1160 includes a first end portion, e.g., a button, 1162, a plurality of balls 1164 and at least one spring 1166 similar to the embodiment of FIG. 5, as well as a second end portion 1161, at least one button spring 1163 positioned between the second end portion 1161 and the outer housing 1124, and a wire 1165. The wire 1165 is attached to and/or extends through the second end portion 1161. For example, the wire 1165 can have a distal end secured (e.g., anchored) in a side wall defined by the ankle module housing, where the sidewall at least partially defines an opening through which the second end portion 1161 moves. The wire 1165 can then extend through (e.g., through an opening in) an opposite side wall that at least partially defines the opening through which the second end portion 1161 moves, as shown in in FIGS. 8A-8B. Starting from an initial closed position as shown in FIG. 8A, to open the spool valve 1150, the user can pull on the wire 1165, thereby causing the wire 1165 to press the second end portion 1161 in and shift the spool valve 1150 to the open position as shown in FIG. 8B. Movement of the second end portion 1161 in toward the housing 1124 compresses the button spring(s) 1163 as shown. The user can then adjust the ankle module 1100 as desired or required. To close the spool valve 1150, the user can push the first end portion 1162 in, as indicated by arrow C in FIG. 8B. Alternatively, the ball lock system 1160 can include a secondary wire 1167 attached to and/or extending through the first end portion 1162, as shown in FIG. 8C. For example, similar to how the wire 1165 is anchored, the secondary wire 1167 can have a distal end secured (e.g., anchored) in a side wall defined by the ankle module housing, where the sidewall at least partially defines an opening through which the first end portion 1162 moves. The secondary wire 1167 can then extend through (e.g., through an opening in) an opposite side wall that at least partially defines the opening through which the first end portion 1162 moves, as shown in in FIG. 8C. To close the spool valve 1150, the user can pull the secondary wire 1167, thereby causing the secondary wire 1167 to press the first end portion 1162 in toward the housing 1124 and shift the spool valve 1150 back to its initial or closed position. The wire(s) 1165, 1167 can be attached to the ankle module 1100, another prosthetic component, and/or a socket attached to the user's residual limb, e.g., via magnets, for storage.

Toe Portion

Prosthetic feet according to the present disclosure advantageously allow for heel height adjustability as described herein. However, in some cases, modifying the heel height alone without adjusting other sections of the prosthetic foot (e.g., the toe region) can place the foot in an unnatural position, which can result in discomfort for the user or a sub-optimal rollover performance during use. Therefore, in some embodiments, prosthetic feet according to the present disclosure advantageously include features that provide metatarsal joint functionality or allow the toe portion to adapt to various heel heights to more closely mimic natural human feet.

Figure 9:
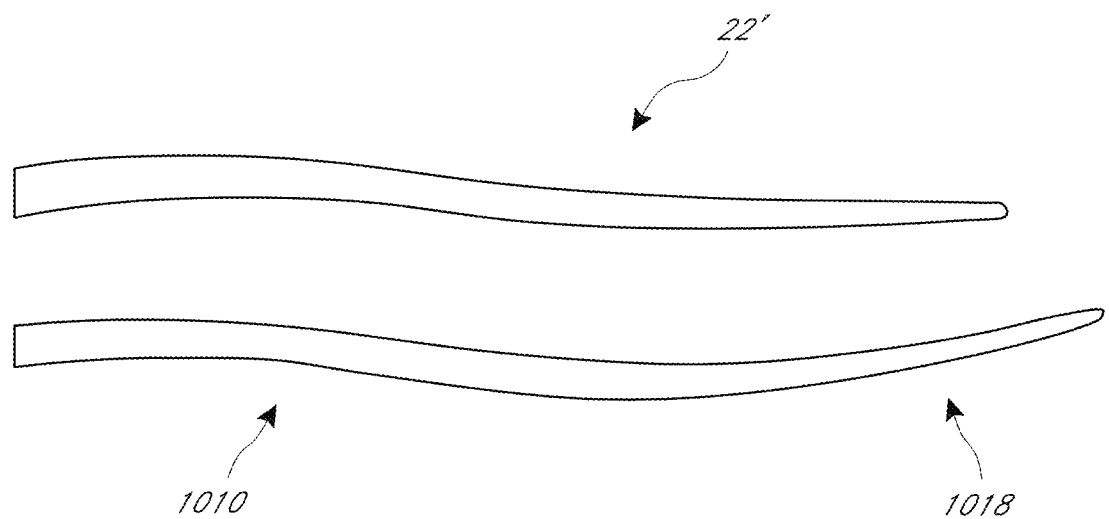
FIG. 9 illustrates a foot member of the prosthetic foot of FIG. 3 that is configured to adapt to varying heel heights compared to a foot member designed for a standard, flat, or neutral heel height.
Figure 10:
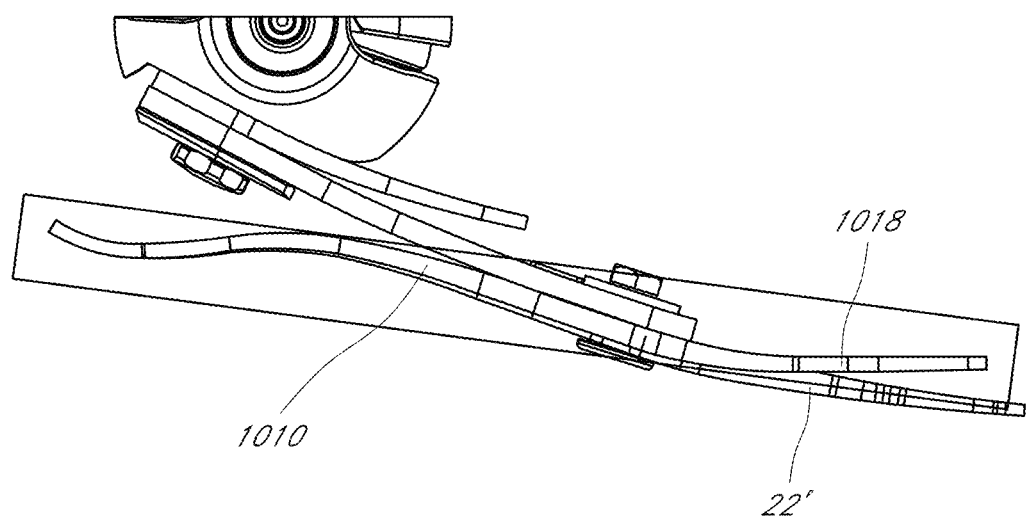
FIG. 10 illustrates the prosthetic foot of FIG. 3 compared to the foot member designed for a standard, flat, or neutral heel height.

The prosthetic foot 1000 of FIG. 3 can include a toe portion 1018 that allows the foot 1000 to accommodate heel height adjustments made at the ankle module 1100. In the illustrated embodiment, the toe portion 1018 curves upward relative to a portion of the foot member, e.g., foot member 1010, proximal to the toe portion 1018. As shown in FIGS. 9-10, the toe portion 1018 is curved more upward compared to a foot member 22' having a toe portion that is flat or has a slight curvature designed for flat or relatively flat shoes. In use, the user's weight shifts to be supported by different areas of the toe portion 1018 as the heel height is adjusted. For example, for a lower heeled shoe and heel height, when standing on a neutral support surface, the user's weight rests at or proximate a proximal end of the toe portion 1018. As the heel height is increased, the user's weight shifts forward to rest on more distal portions of the toe portion 1018. The toe portion 1018 therefore allows the lower foot member 1010 and/or prosthetic foot 1000 to automatically adapt to varying heel heights without the need for separate adjustment. The curvature of the toe portion 1018 can advantageously allow the foot 1000 to achieve a better fit in various shoes, including high heeled shoes. The curvature of the toe portion 1018 can also or alternatively help reduce wear on the foot 1000, e.g., the foot member 1010, during use. In some embodiments, the curvature of the toe portion 1018 can be selected to allow the toe portion 1018 to adapt to varying heel heights while providing sufficient push off during the toe off portion of the gait cycle.

Figure 11:
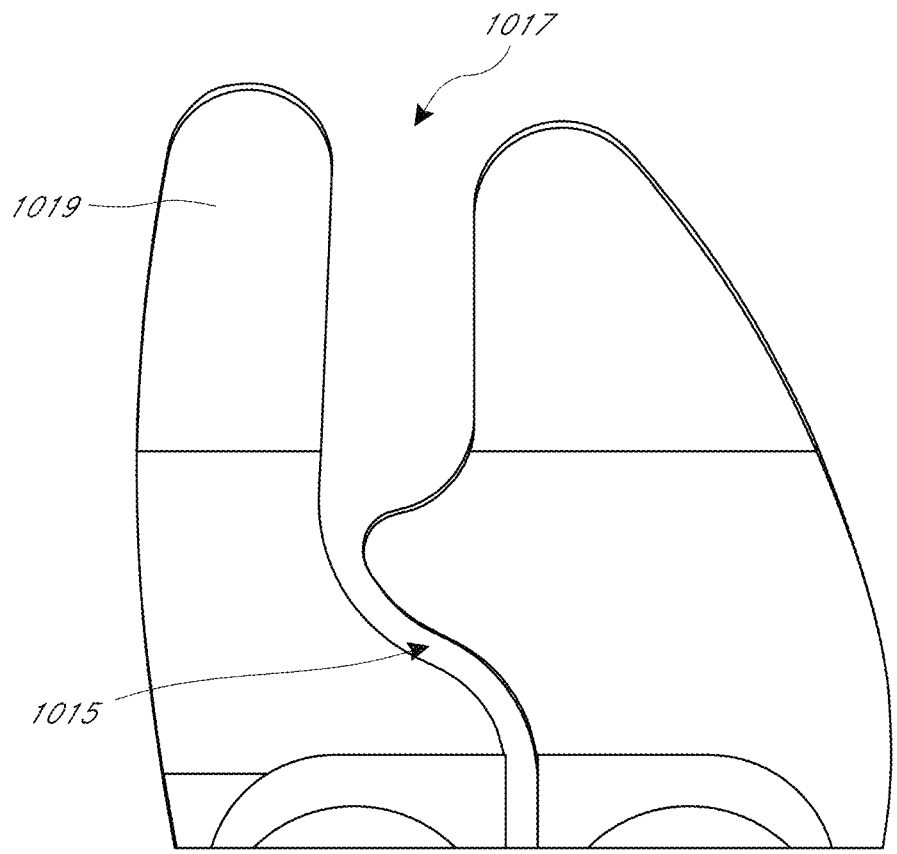
FIG. 11 illustrates a top close-up view of a toe portion of a prosthetic foot.

In some embodiments, the toe portion 1018 includes a generally U-shaped cut-out portion, slot, or gap 1017 extending inwardly or proximally from a distal toe end, for example as shown in FIGS. 11-14. In some embodiments, the cut-out 1017 is positioned toward a medial side of a longitudinal axis of the lower foot member 1010, but is spaced from a medial edge of the lower foot member 1010. The cut-out 1017 gives the lower foot member 1010 a "sandal toe" appearance and/or function and defines a structural "big toe" 1019. The cut out portion 1017 can receive a strap of a sandal. In the illustrated embodiment, the big toe 1019 is longer (e.g., extends further distally) than the remaining "toes" or the remainder of the toe portion 1018. The lower foot member 1010 can also include a split 1015 that at least partially extends substantially along the longitudinal axis of the lower foot member 1010 to the cut-out 1017. As shown in FIG. 11, the transition between the split 1015 and the cut-out 1017 can be rounded, or can lack sharp corners. This can advantageously reduce delamination of the toe portion 1018 during manufacturing and/or failure of the toe portion 1018 in use.

Figure 12:
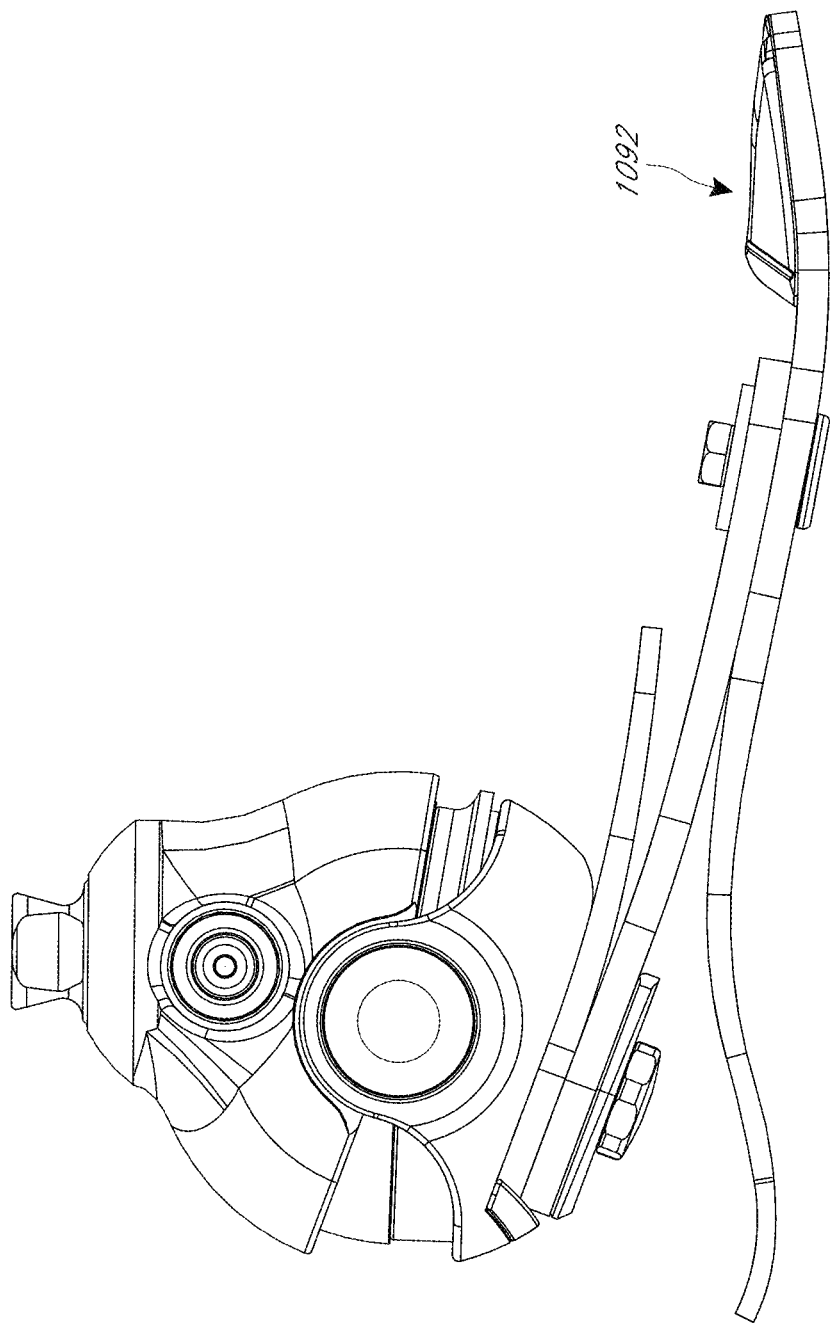
FIG. 12 illustrates a side view of an example embodiment of a prosthetic foot having heel height adjustability.
Figure 13:
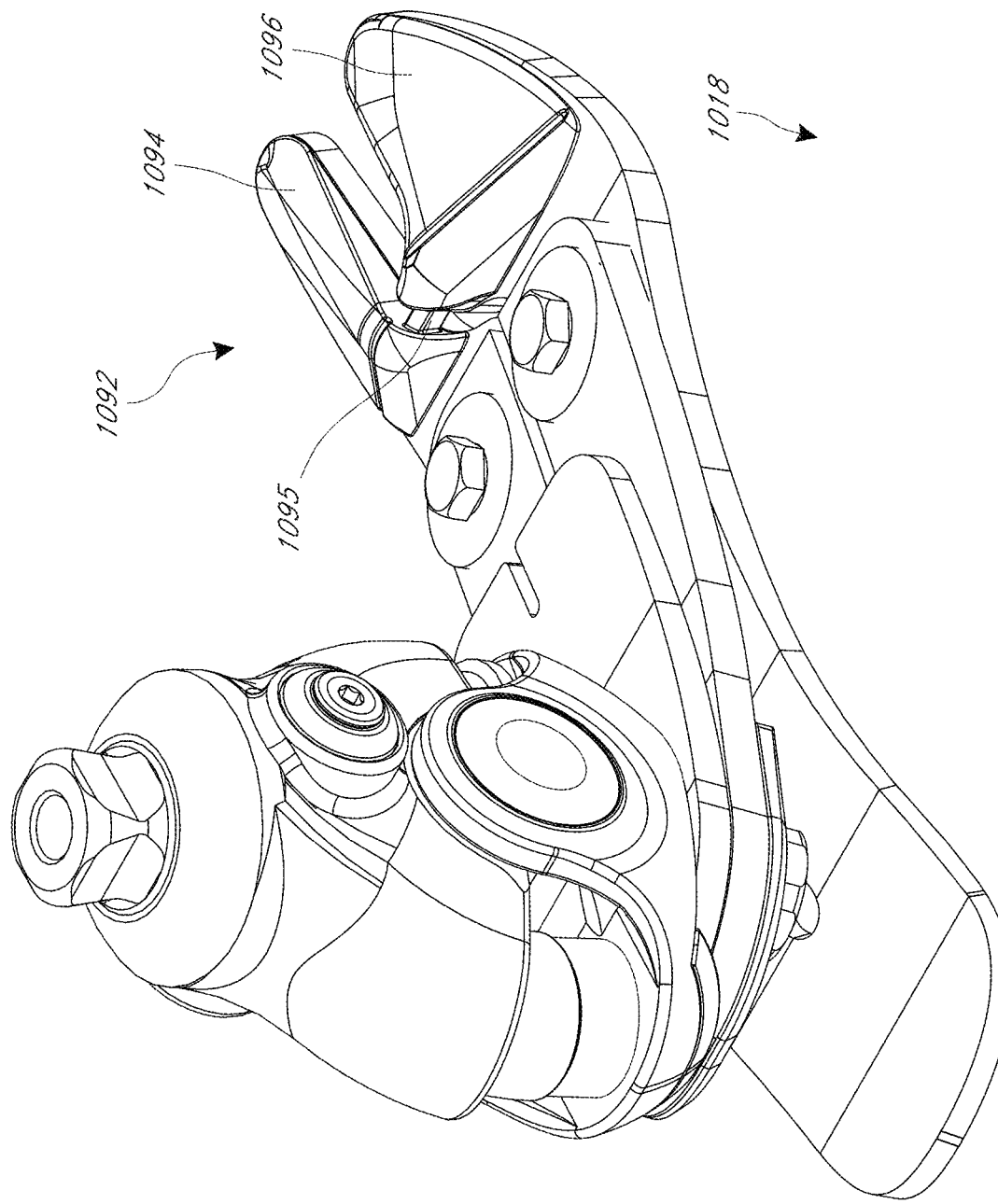
FIG. 13 illustrates a rear-side perspective view of the prosthetic foot of FIG. 12.
Figure 14:
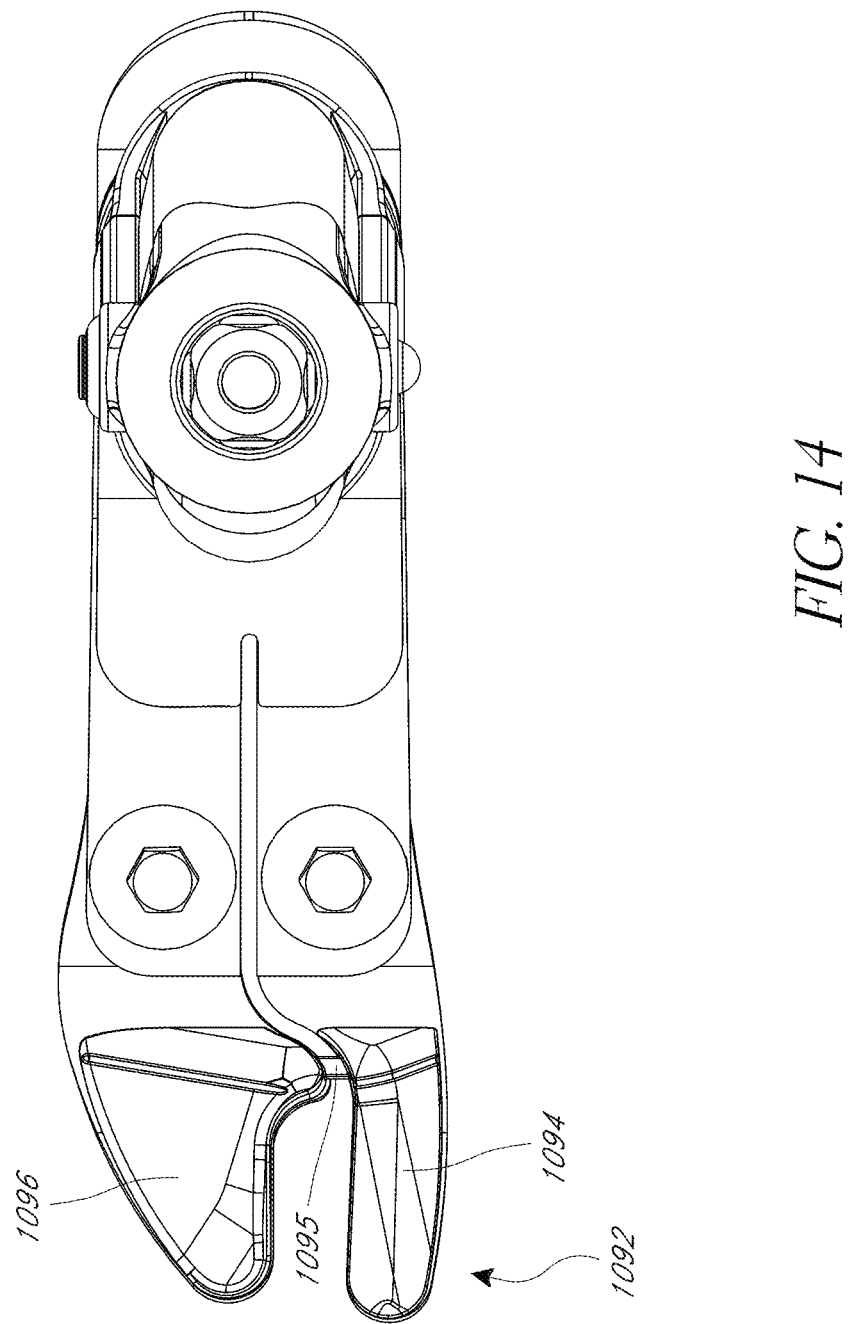
FIG. 14 illustrates a top view of the prosthetic foot of FIG. 12.

In some embodiments, the prosthetic foot 1000 includes a toe piece 1092 coupled to a top surface of at least a portion of the toe portion 1018, as shown in FIGS. 12-14. The toe piece 1092 is sized, shaped, and/or otherwise designed to follow the outer contours of the toe portion 1018. The toe piece 1092 can be made of a resilient material, e.g., rubber. In the illustrated embodiment, the toe piece 1092 includes a big toe portion 1094 that overlies and/or is coupled to the big toe 1019 of the lower foot member 1010 and a body portion 1096 that overlies and/or is coupled to the remainder of the toe portion 1018. The big toe portion 1094 can be coupled to the body portion 1096 by a bridge piece 1095 as shown. The toe piece 1092 has a thickness or height (e.g., tapering toward the front end such that the front end is thinner than a rear end of the toe piece 1092) selected to fill or at least partially fill space between the toe portion 1018 of the lower foot member 1010 and an inner surface of a cosmesis, for example as described herein, if and when the prosthetic foot 1000 is disposed in the cosmesis for use. The toe piece 1092 can therefore reduce relative motion between the toe portion 1018 and cosmesis in use (e.g., by exerting a friction force between a surface of the toe piece 1092 and an inner upper surface of the cosmesis), which can advantageously reduce wear on the cosmesis.

Figure 15A:
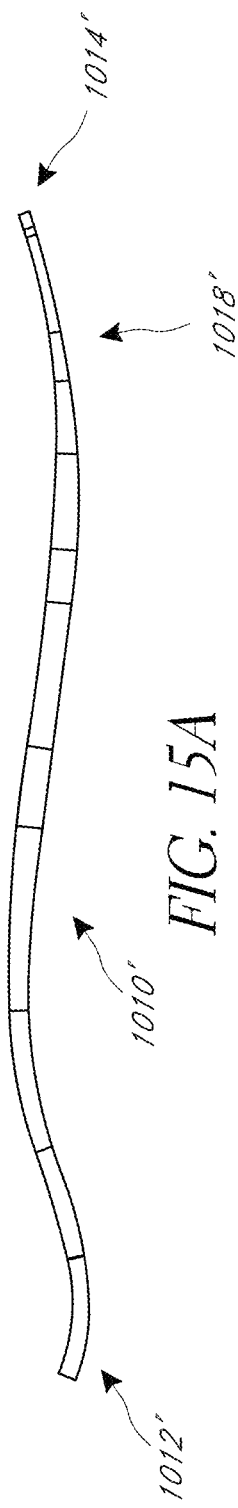
FIG. 15A illustrates an example embodiment of a foot member having a toe portion configured to adapt to varying heel heights.
Figure 15B:
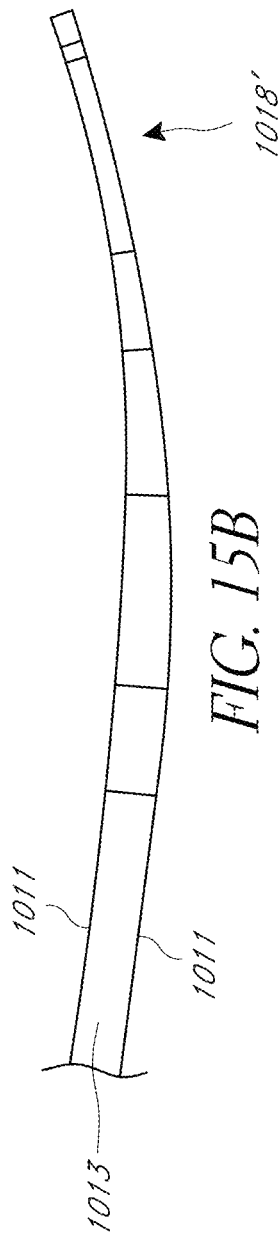
FIG. 15B illustrates a close-up view of a toe portion of the foot member of FIG. 15A.

FIGS. 15A-15B illustrate another example embodiment of a foot member 1010' having a toe portion 1018' that adapts to varying heel heights. The toe portion 1018' includes glass fiber. The glass fiber can advantageously increase the flexibility of the toe portion 1018'. In the illustrated embodiment, the toe portion 1018' is curved upward similar to the toe portion 1018 shown in FIGS. 9-10. In some embodiments, the toe portion 1018' is flat or has a curvature similar to the foot member 22' shown in FIGS. 9-10 or other available foot members designed for flat or relatively flat shoes. In some embodiments, the foot member 1010' is made of a layup including one or more layers of glass fiber or a glass composite that extend from the proximal end 1012' to the distal end 1014' and one or more layers of carbon or a carbon composite that extend from the proximal end 1012' to a point proximal and adjacent or proximate to a proximal end of the toe portion 1018'. For example, as shown in FIG. 15B, the foot member 1010' can include upper and lower portions 1011 that include one or more layers of glass fiber that extend the full length of the foot member 1010' and a central portion 1013 of carbon fiber that extends to a point proximal to the toe portion 1018'. In some embodiments, the layers of glass fiber may not extend to the proximal end 1012'.

Cosmesis

In some embodiments, a prosthetic foot that allows for heel height adjustability as described herein can be disposed in a cosmesis configured to resemble a natural human foot. However, a conventional cosmesis may not allow for heel height adjustability or may wrinkle when the heel height is adjusted, which may impede the foot from fully adjusting to the desired heel height and/or may make the cosmesis less aesthetically pleasing.

Figure 16:
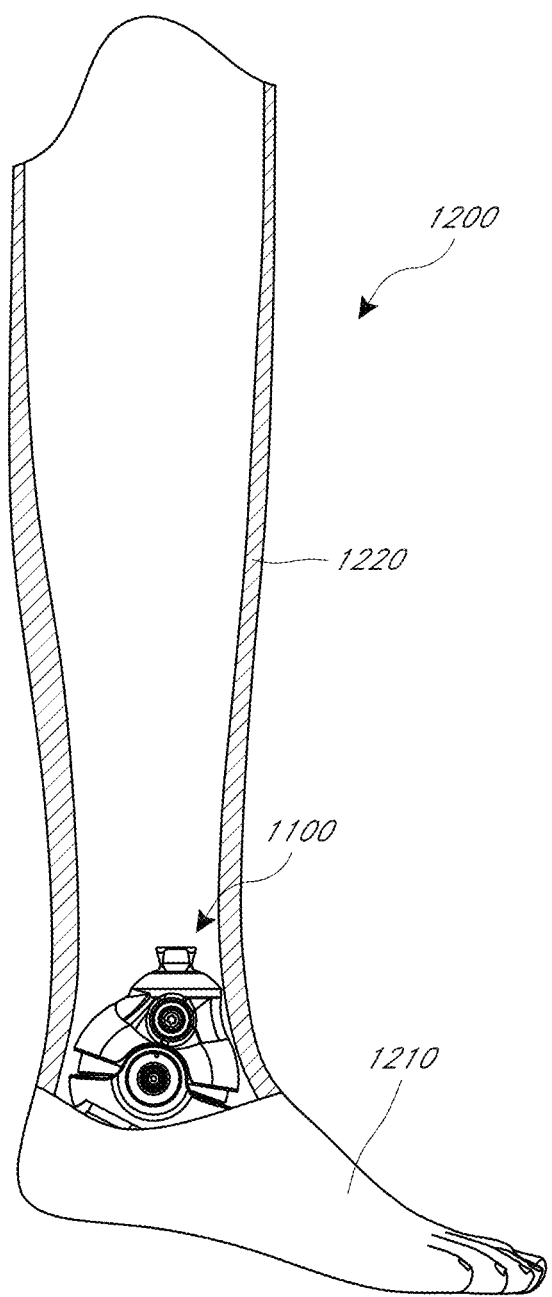
FIG. 16 illustrates the prosthetic foot of FIG. 3 disposed in an example embodiment of a cosmesis including a foot portion and calf portion.
Figure 17:
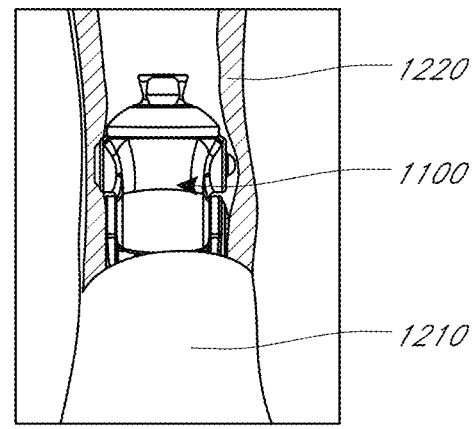
FIG. 17 illustrates a partial front sectional view of the prosthetic foot and cosmesis of FIG. 16.
Figures 21A, 21B:
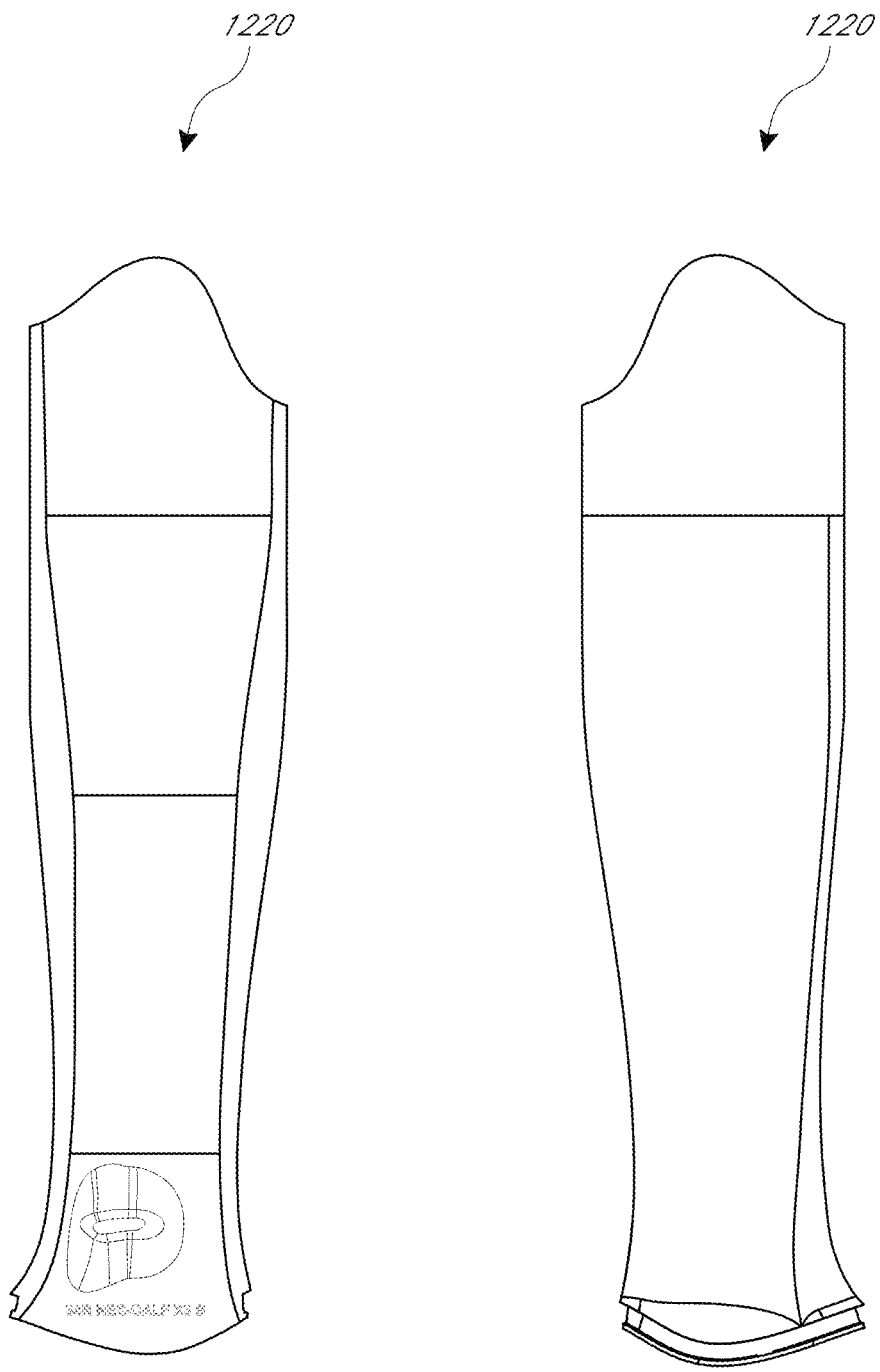
FIG. 21A illustrates a front view of the calf portion of the cosmesis of FIG. 8.
FIG. 21B illustrates a rear view of the calf portion of the cosmesis of FIG. 8.
Figure 22:
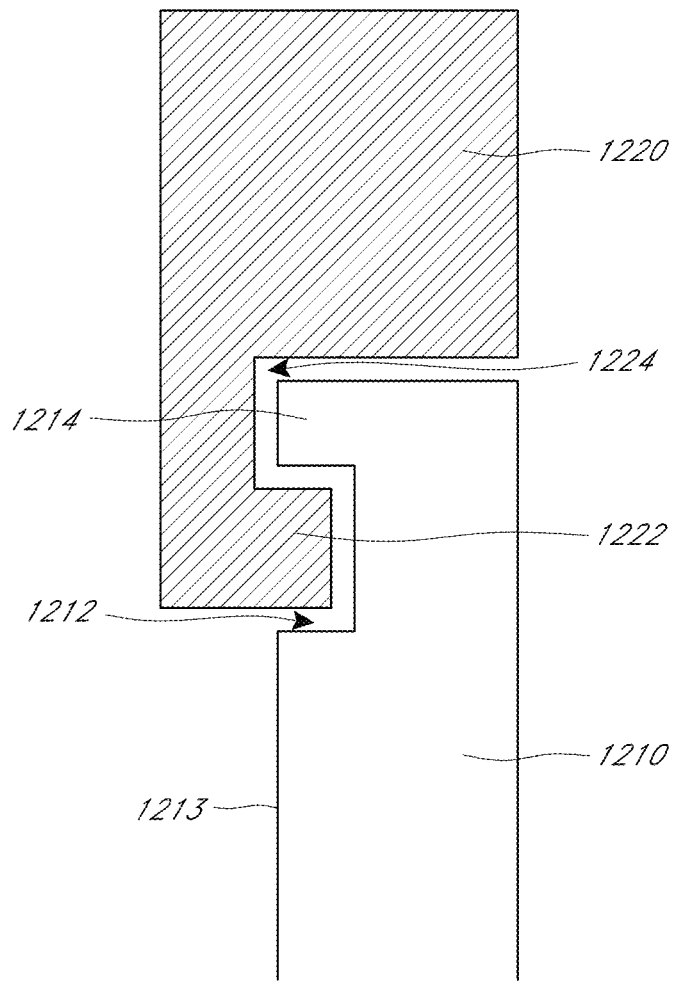
FIG. 22 illustrates a schematic longitudinal cross-sectional view of a connection between a calf cosmesis and a foot cosmesis.

FIGS. 16-17 illustrate an example embodiment of a cosmesis 1200 that includes a foot portion 1210 and a calf portion 1220 (also shown in FIGS. 21A-21B). The foot 1210 and calf 1220 portions can be used together, as shown in FIGS. 16-17, or either portion can be used alone or separately. When used together, a prosthetist glues or otherwise couples the foot 1210 and calf 1220 portions together, for example, as is done with some conventional cosmeses. In some embodiments, instead of the connection between the calf portion 1220 and foot portion 1210 being at or between the top edge or surface of the foot portion 1210 and the bottom edge or surface of the calf portion 1220, the connection can be located along an inner surface of the foot portion 1210. For example, as shown in FIG. 22, the foot portion 1210 can include a recess 1212 defined on or in an inner surface 1213 proximate the upper edge or surface of the foot portion 1210. The recess 1212 is sized, shaped, and/or otherwise designed to receive a lower lip 1222 of the calf portion 1220. The calf portion 1220 can include a recess 1224 proximate the lower edge or surface of the calf portion 1220 to receive an upper lip 1214 of the foot portion 1210 as shown. Accordingly, the calf cosmesis can be coupled with the foot cosmesis so that no portion of the connection is visible while in use, and so the combined calf and foot cosmesis assembly appears seamless.

In some embodiments, the junction between the calf portion 1220 and foot portion 1210 of the cosmesis 1200 is lower than in some conventional covers. In some embodiments, the junction or seam is covered by the shoe when the cosmesis is disposed in a shoe. In some embodiments, the junction or seam is at least partially positioned or curves below the location of the malleoli on a natural human foot and/or below the location of the ankle module. The junction or seam may be relatively stiff compared to other areas of the cosmesis 1200. Positioning the junction below the location of the ankle module can advantageously allow the portion of the cosmesis 1200 around the ankle module to be relatively more flexible than the junction to allow the cosmesis 1200 to stretch and/or otherwise accommodate rotation or other movement at the ankle. In some embodiments, the cosmesis is made of EVA. FIGS. 16-17 illustrate the cosmesis 1200 in combination with the prosthetic foot 1000. However, either of both of the foot portion 1210 and calf portion 1220 can be adapted for use with other prosthetic feet designs.

In some embodiments, a wall of the calf portion 1220 is thinner in the region(s) designed to be adjacent or surrounding the first end portion or button 1162 and/or second end portion 1161 when the prosthetic foot is disposed in the cosmesis 1200 (or another cosmesis including calf portion 1220). The thinner region can allow the user to more easily press or access the first end portion 1162 and/or second end portion 1161 through the calf portion 1220 to adjust the heel height of the prosthetic foot 1000. In some embodiments, portions of the wall of the calf portion 1220 designed to be adjacent or proximate the front and/or rear of the ankle module 1100 when the prosthetic foot is disposed in the cosmesis 1200 (or another cosmesis including calf portion 1220) are thicker than a remainder of the calf portion 1220.

These thickened portions can help inhibit or reduce the likelihood of wrinkling of the calf portion 1220 during use and/or as the ankle module 1100 is adjusted. The calf portion 1220 can be provided to a prosthetist such that an outer surface of the calf portion 1220 is ready for use, and the prosthetist can grind an inner surface of the calf portion 1220 as needed, for example, to thin the region(s) adjacent or surrounding the first end portion 1162 and/or second end portion 1161 and/or to make space at or proximate an upper end of the calf portion 1220 to accommodate a socket coupled to the user's residual limb.

As shown in FIGS. 16 and 18, the foot portion 1210 can have an intermediate heel height, for example, approximately 1 cm-5 cm, approximately 2 cm-4 cm, or approximately 3 cm, built into the cosmesis so that the cosmesis has an intermediate heel height in a neutral position. The cosmesis can then adjust to a range of heel heights from a flat foot or minimal heel height position, e.g., 0 cm, up to a height of, for example, around 7 cm with little deformation.

Figure 19:
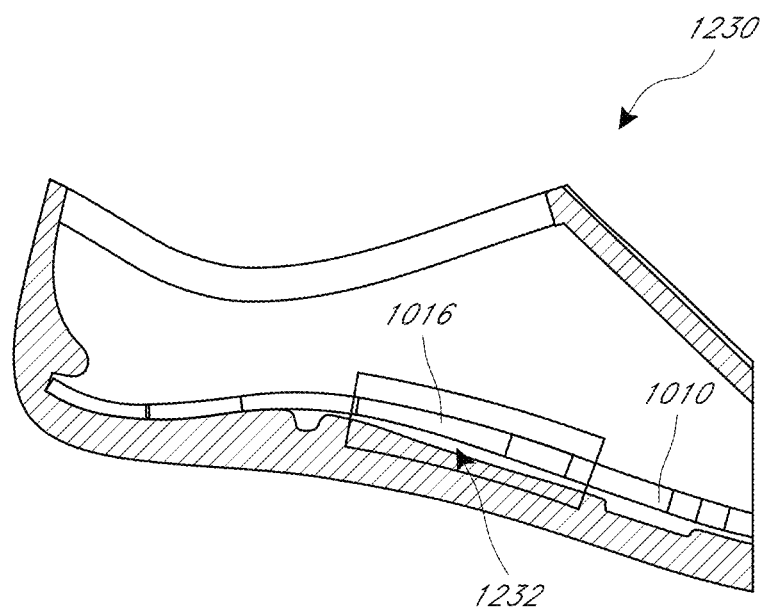
FIG. 19 illustrates a longitudinal cross-sectional view of an example embodiment of a foot cosmesis.

FIG. 19 illustrates another example embodiment of a foot cosmesis 1230 or foot portion of a cosmesis. In some embodiments, the cosmesis 1230 is design for use with the prosthetic foot 1000 shown in and described with respect to FIG. 3. In some embodiments, the cosmesis 1230 can be adapted for use with other prosthetic foot designs or configurations. As shown, when the prosthetic foot, e.g., prosthetic foot 1000, is disposed in the cosmesis 1230 and the user is standing on a support surface in a neutral position with the prosthetic foot adjusted to a neutral heel height (e.g., a minimum heel height or an intermediate heel height in an embodiment in which an intermediate heel height is built into the cosmesis), there is a gap 1232 between a bottom surface of the arch region 1016 of the foot member, e.g., lower foot member 1010, and an inner surface of a sole portion of the cosmesis 1230. The gap 1232 advantageously allows the cosmesis 1230 to deform to adapt to shoes having various heel heights, for example, with reduced, minimal, or no wrinkling. In some embodiments, as the heel height is increased the foot member flexes toward the inner surface of the sole portion of the cosmesis 1230, decreasing and eventually closing the gap 1232.

Figure 20:
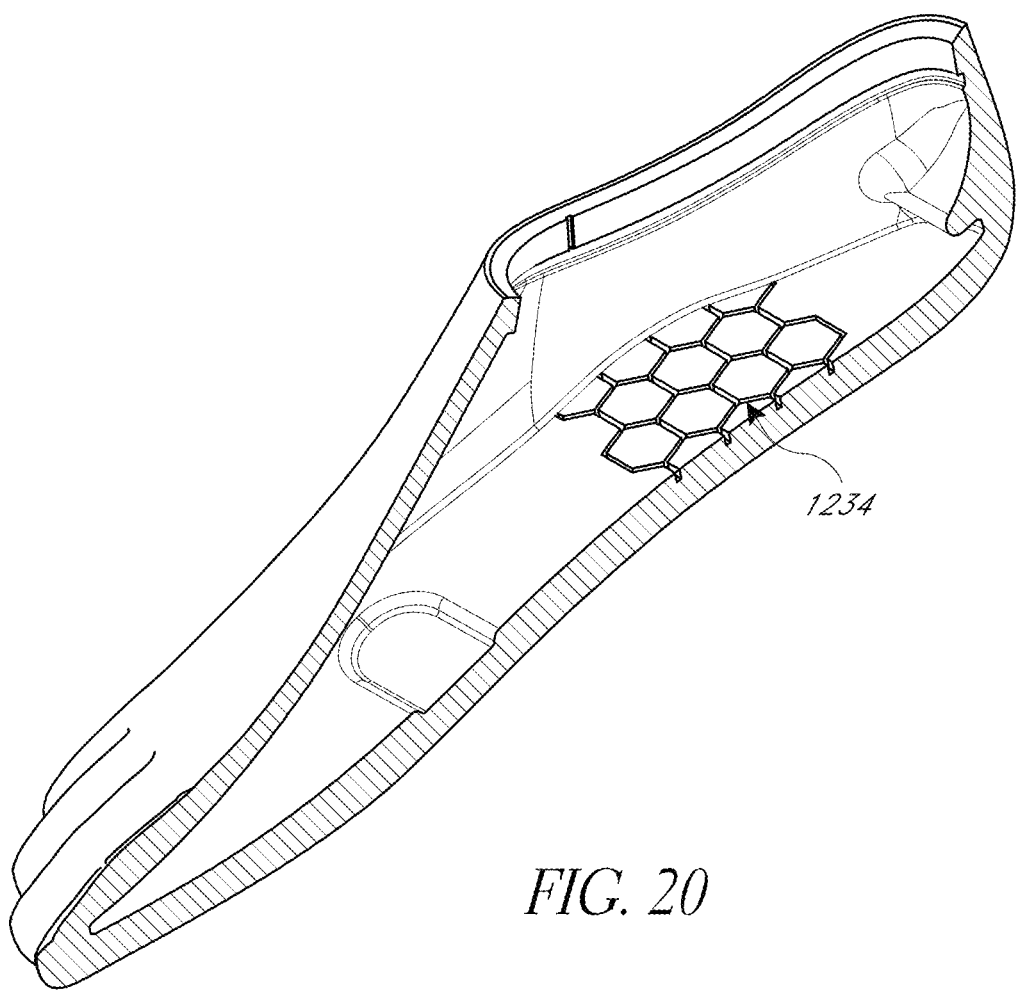
FIG. 20 illustrates a partial top-side perspective longitudinal cross-sectional view of an example embodiment of a foot cosmesis.

Instead of or in addition to the gap 1232, the arch region of the inner surface of the sole portion of the cosmesis 1230 can include a region 1234 of channels or recesses formed in the inner surface. The channels or recesses can be arranged in a honeycomb pattern, for example as shown in FIG. 20. The region 1234 of channels or recesses can allow the sole portion to flex to adapt to shoes having various heel heights.

Vacuum Socket Attachment

In some embodiments, various feet and/or ankle modules shown and described herein can be configured to be compatible with vacuum suspension systems. Such a system generates negative pressure within a prosthetic socket to improve the fit and stability of the socket relative to the residual limb. The distal end of the residual limb typically has more soft tissue compared to the area closer to the knee. The distal end is therefore more susceptible to volume fluctuations throughout the day, which can impede stabilization and suspension of the socket. A vacuum suspension system that can be used with the feet described herein can therefore apply a vacuum to the distal end of the residual limb to improve stability and suspension. The system can include a frame coupled to the foot and a membrane disposed on or between parts of the frame. When the user places weight on the heel of the foot, the membrane expands, which causes air to be drawn out of the socket to create and maintain the vacuum. Additional details regarding such systems are shown and described in U.S. Publications 2013/0289742, 2013/0289741, and 2013/0221544 and U.S. Design U.S. Pat. Nos. D711,510 and D718,861, the entireties of which are hereby incorporated by reference herein.

Although this disclosure has been described in the context of certain embodiments and examples, it will be understood by those skilled in the art that the disclosure extends beyond the specifically disclosed embodiments to other alternative embodiments and/or uses and obvious modifications and equivalents thereof. In addition, while several variations of the embodiments of the disclosure have been shown and described in detail, other modifications, which are within the scope of this disclosure, will be readily apparent to those of skill in the art. It is also contemplated that various combinations or sub-combinations of the specific features and aspects of the embodiments may be made and still fall within the scope of the disclosure. For example, features described above in connection with one embodiment can be used with a different embodiment described herein and the combination still fall within the scope of the disclosure. It should be understood that various features and aspects of the disclosed embodiments can be combined with, or substituted for, one another in order to form varying modes of the embodiments of the disclosure. Thus, it is intended that the scope of the disclosure herein should not be limited by the particular embodiments described above. Accordingly, unless otherwise stated, or unless clearly incompatible, each embodiment of this invention may comprise, additional to its essential features described herein, one or more features as described herein from each other embodiment of the invention disclosed herein.

Features, materials, characteristics, or groups described in conjunction with a particular aspect, embodiment, or example are to be understood to be applicable to any other aspect, embodiment or example described in this section or elsewhere in this specification unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

Furthermore, certain features that are described in this disclosure in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations, one or more features from a claimed combination can, in some cases, be excised from the combination, and the combination may be claimed as a subcombination or variation of a sub combination.

Moreover, while operations may be depicted in the drawings or described in the specification in a particular order, such operations need not be performed in the particular order shown or in sequential order, or that all operations be performed, to achieve desirable results. Other operations that are not depicted or described can be incorporated in the example methods and processes. For example, one or more additional operations can be performed before, after, simultaneously, or between any of the described operations. Further, the operations may be rearranged or reordered in other implementations. Those skilled in the art will appreciate that in some embodiments, the actual steps taken in the processes illustrated and/or disclosed may differ from those shown in the figures. Depending on the embodiment, certain of the steps described above may be removed, others may be added. Furthermore, the features and attributes of the specific embodiments disclosed above may be combined in different ways to form additional embodiments, all of which fall within the scope of the present disclosure. Also, the separation of various system components in the implementations described above should not be understood as requiring such separation in all implementations, and it should be understood that the described components and systems can generally be integrated together in a single product or packaged into multiple products.

For purposes of this disclosure, certain aspects, advantages, and novel features are described herein. Not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Conditional language, such as "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without user input or prompting, whether these features, elements, and/or steps are included or are to be performed in any particular embodiment.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain embodiments, the terms "generally parallel" and "substantially parallel" refer to a value, amount, or characteristic that departs from exactly parallel by less than or equal to 15 degrees, 10 degrees, 5 degrees, 3 degrees, 1 degree, 0.1 degree, or otherwise.

The scope of the present disclosure is not intended to be limited by the specific disclosures of preferred embodiments in this section or elsewhere in this specification, and may be defined by claims as presented in this section or elsewhere in this specification or as presented in the future. The language of the claims is to be interpreted broadly based on the language employed in the claims and not limited to the examples described in the present specification or during the prosecution of the application, which examples are to be construed as non-exclusive.

What is claimed is:

1. A prosthetic foot comprising:
an ankle module configured to be coupled to a lower limb member;
an elongate foot member extending from a proximal end to a distal end, the proximal end coupled to the ankle module;
an elongate lower foot member extending from a proximal end to a distal end, wherein the lower foot member is positioned below and coupled to the foot member and the lower foot member extends distally beyond the distal end of the foot member to form a toe region, and
a toe piece coupled to a top surface of the toe region, the toe piece tapering toward a front end of the toe piece, a distal end of the toe piece terminating at the distal end of the lower foot member so that the distal ends of the toe piece and the lower foot member define a distal end of the toe region, the toe piece comprising a different material than the elongate lower foot member, wherein the ankle module is selectively actuatable to adjust an angle between the prosthetic foot and the lower limb member to allow for adjustment of a heel height of the prosthetic foot,
wherein the toe region curves upward and is configured to adapt to various heel heights of the prosthetic foot, and
wherein the toe region comprises a generally U-shaped cut-out extending proximally from the distal end of the lower foot member, the lower foot member comprises a split extending at least partially along a longitudinal axis of the lower foot member to the cut-out, and a transition between the split and the cut-out is rounded.

2. The prosthetic foot of claim 1, wherein the ankle module comprises a hydraulic adjustment mechanism.

3. The prosthetic foot of claim 1, wherein the toe region comprises glass fiber.

4. The prosthetic foot of claim 1, wherein the lower foot member comprises one or more layers of glass fiber extending from the proximal end to the distal end and one or more layers of carbon fiber extending from the proximal end to a point proximal of the distal end.

5. The prosthetic foot of claim 1, further comprising an upper foot member extending from a proximal end to a distal end, the upper foot member positioned above the foot member and the proximal end coupled to the proximal end of the foot member and the ankle module.

6. The prosthetic foot of claim 5, wherein the distal end of the upper foot member is separated from the foot member by a gap when the prosthetic foot is at rest in a neutral position.

7. The prosthetic foot of claim 1, wherein the toe piece is shaped to follow an outer contour of the toe region of the lower foot member.

8. The prosthetic foot of claim 1, wherein the toe piece is coupled to only the top surface of the toe region of the lower foot member.

9. The prosthetic foot of claim 1, wherein a top surface of the toe piece is contoured to fill a gap between a top surface of the lower foot member and an inner surface of a cosmesis.

10. The prosthetic foot of claim 1, wherein the toe piece comprises a big toe portion and a body portion.

11. The prosthetic foot of claim 10, wherein the big toe portion and the body portion of the toe piece are connected by a bridge piece.

12. The prosthetic foot of claim 1, wherein the different material of the toe piece comprises rubber.

13. A prosthetic foot comprising:
an ankle module configured to be coupled to a lower limb member;
an elongate foot member extending from a proximal end to a distal end, the proximal end coupled to the ankle module;
an elongate lower foot member extending from a proximal end to a distal end, wherein the lower foot member is positioned below and coupled to the foot member and the lower foot member extends distally beyond the distal end of the foot member to form a toe region, and
a toe piece coupled to a top surface of the toe region, the toe piece tapering toward a front end of the toe piece, a distal end of the toe piece terminating at the distal end of the lower foot member so that the distal ends of the toe piece and the lower foot member define a distal end of the toe region, the toe piece comprising a different material than the elongate lower foot member, wherein the toe piece comprises a big toe portion and a body portion,
wherein the ankle module is selectively actuatable to adjust an angle between the prosthetic foot and the lower limb member to allow for adjustment of a heel height of the prosthetic foot, and
wherein the toe region curves upward and is configured to adapt to various heel heights of the prosthetic foot.

14. The prosthetic foot of claim 13, wherein the ankle module comprises a hydraulic adjustment mechanism.

15. The prosthetic foot of claim 13, wherein the toe region comprises glass fiber.

16. The prosthetic foot of claim 13, wherein the lower foot member comprises one or more layers of glass fiber extending from the proximal end to the distal end and one or more layers of carbon fiber extending from the proximal end to a point proximal of the distal end.

17. The prosthetic foot of claim 13, further comprising an upper foot member extending from a proximal end to a distal end, the upper foot member positioned above the foot member and the proximal end coupled to the proximal end of the foot member and the ankle module.

18. The prosthetic foot of claim 13, wherein a top surface of the toe piece is contoured to fill a gap between a top surface of the lower foot member and an inner surface of a cosmesis.

19. The prosthetic foot of claim 13, wherein the big toe portion and the body portion of the toe piece are connected by a bridge piece.

20. The prosthetic foot of claim 13, wherein the different material of the toe piece comprises rubber.

* * * * *